(12) United States Patent
Hwang et al.

(10) Patent No.: US 9,945,914 B2
(45) Date of Patent: Apr. 17, 2018

(54) SYSTEMS, APPARATUS, AND METHODS OF NONLINEAR TERAHERTZ (THZ) MAGNETIC RESONANCE MEASUREMENT

(71) Applicants: Harold Young Hwang, Cambridge, MA (US); Jian Lu, Medford, MA (US); Yaqing Zhang, Cambridge, MA (US); Benjamin K. Ofori-Okai, Cambridge, MA (US); Keith A. Nelson, Newton, MA (US); Xian Li, Cambridge, MA (US)

(72) Inventors: Harold Young Hwang, Cambridge, MA (US); Jian Lu, Medford, MA (US); Yaqing Zhang, Cambridge, MA (US); Benjamin K. Ofori-Okai, Cambridge, MA (US); Keith A. Nelson, Newton, MA (US); Xian Li, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/600,029

(22) Filed: May 19, 2017

(65) Prior Publication Data
US 2017/0336482 A1 Nov. 23, 2017

Related U.S. Application Data

(60) Provisional application No. 62/338,843, filed on May 19, 2016.

(51) Int. Cl.
*G01R 33/26* (2006.01)
*G01R 33/60* (2006.01)

(52) U.S. Cl.
CPC ............ *G01R 33/26* (2013.01); *G01R 33/60* (2013.01)

(58) Field of Classification Search
CPC ................................ G01R 33/26; G01R 33/60
(Continued)

(56) References Cited

U.S. PATENT DOCUMENTS 4,626,783 A 12/1986 Ohuchi
8,264,693 B2 * 9/2012 Stoica ................ G01R 33/1284
356/502
(Continued)

OTHER PUBLICATIONS

International Search Report and Written Opinion dated Aug. 10, 2017 from International Application No. PCT/US2017/033613, 13 pages.
(Continued)

*Primary Examiner* — Melissa Koval
*Assistant Examiner* — Rahul Maini
(74) *Attorney, Agent, or Firm* — Cooley LLP

(57) ABSTRACT

A nonlinear terahertz (THz) spectroscopy technique uses a sample illuminated by two THz pulses separately. The illumination generates two signals $B_A$ and $B_B$, corresponding to the first and second THz pulse, respectively, after interaction with the sample. The interaction includes excitation of at least one ESR transition in the sample. The sample is also illuminated by the two THz pulses together, with an inter-pulse delay τ, generating a third signal $B_{AB}$. A nonlinear signal BNL is then derived via $B_{NL}=B_{AB}-B_A-B_B$. This nonlinear signal $B_{NL}$ can be then processed (e.g., Fourier transform) to study the properties of the sample.

23 Claims, 21 Drawing Sheets

(58) Field of Classification Search
USPC .......................................... 324/304; 356/502
See application file for complete search history.

(56) References Cited

U.S. PATENT DOCUMENTS

| | | |
|---|---|---|
| 2009/0066948 A1 | 3/2009 | Karpowicz et al. |
| 2009/0206263 A1 | 8/2009 | Rahman |
| 2009/0225313 A1 | 9/2009 | Umetsu |
| 2013/0154611 A1 | 6/2013 | Pate et al. |

OTHER PUBLICATIONS

Acbas, G. et al., Optical measurements of long-range protein vibrations. Nature Comm. 5:3076, 7 pages (2014).
Baek, S.H. et al., Ferroelastic switching for nanoscale non-volatile magnetoelectric devices. Nature Mater. 9, 309-314 (2010).
Bajaj, V.S. et al., Functional and shunt states of bacteriorhodopsin resolved by 250 GHz dynamic nuclear polarization-enhanced solid-state Nmr. Proc. Nat. Acad. Sci. USA 106, 9244-9249 (2009).
Boca, R. et al., Simple Mononuclear Cobalt(II) Complex: A Single-Molecule Magnet Showing Two Slow Relaxation Processes. Inorg. Chem. 53(5), 2367-2369 (2014).
Borbat, P.P. et al., Electron spin resonance in studies of membranes and proteins. Science 291, 266-269 (2001).
Chumak, A.V. et al., Magnon spintronics, Nature Phys. II, 453-461 (2015).
Craig, G.A. et al., 3d single ion magnets. Chem. Soc. Rev. 44, 2135 (2015).
Dreiser, J. et al., Frequency-domain Fourier transform terahertz spectroscopy of the single-molecule magnet $(NEt_4)[Mn_2(5-Brsalen)_2(MeOH)_2Cr(Cn)_6]$. Chem. Eur. J. 17, 7492-7498 (2011).
Eerenstein, W. et al., Multiferroic and magnetoelectric materials. Nature 442, 759-765 (2006).
Fleury, P.A. et al., Scattering of light by one- and two-magnon excitations. Phys. Rev. 166, 514-530 (1968).
Hahn, E.L., Spin Echos. Phys. Rev. 80, 580, 22 pages (1950).
Hahn, S.E. et al., Inelastic neutron scattering studies of $YFeO_3$. Phys. Rev. B 89, 014420-1-6 (2014).
He, Y. et al., Evidence of protein collective motions on the picosecond timescale. Biophys. J. 100(4), 1058-1065 (2011).
Herrmann, G.F., Magnetic Resonances and susceptibility in orthoferrites. Phys. Rev. 133, A1334, 11 pages (1964).
Herrmann, G.F., Resonance and high frequency susceptibility in canted antiferromagnetic substances. J Phys. Chem. Solids 24, 597-606 (1963).
Hirori, H. et al., Single-cycle terahertz pulses with amplitudes exceeding 1 MY/cm generated by optical rectification in $LiNbO3$. Appl. Phys. Lett. 98, 091106-1-3 (2011).
Idesicova, M. et al., Zero-field splitting in pseudotetrahedral Co(II) complexes: a magnetic, high-frequency and -field EPR, and Computational Study. Inorg. Chem. 53, 9409-9417 (2013).
Kampfrath, T. et al., Coherent terahertz control of anti ferromagnetic spin waves. Nature Photon. 5, 31-34 (2011).

Kampfrath, T. et al., Resonant and nonresonant control over matter and light by intense terahertz transients. Nature Photon. 7, 680-690 (2013).
Kimel, A.V. et al., Inertia-driven spin switching in antiferromagnets. Nature Phys. 5, 727-731 (2009).
Kiselev, S.I. et al., Microwave oscillations of a nanomagnet driven by a spin-polarized current. Nature 425, 380-383 (2003).
Koopens, F.H.L. et al., Driven coherent oscillations of a single electron spin in a quantum dot. Nature 442, 766-771 (2006).
Lambert, C. H. et al., All-optical control of ferromagnetic thin films and nanostructures. Science 345, 1337-1340 (2014).
Li, T. et al., Femtosecond switching of magnetism via strongly correlated spin-charge quantum excitations. Nature 496, 69-73 (2013).
Lutgemeier, H. et al., NMR observation of the spin structure and field induced spin reorientation in $YfeO3$. J. Magn. Magn. Mater. 21, 289-296 (1980).
Mathies, G. et al., High-frequency EPR study of the high-spin FeII complex $Fe[(SPPh2)2N]2$, J. Magn. Reson. 224, 94-100 (2012).
Milios, C.J. et al., A record anisotropy barrier for a single-molecule magnet. J. Am. Chem. Soc. 129(10), 2754-2755 (2007).
Morello, A. et al., Pairwise decoherence in coupled spin qubit networks. Phys. Rev. Lett. 91, 207206-1-4 (2006).
Mukai, Y. et al., Nonlinear magnetization dynamics of anti ferromagnetic resonance induced by intense terahertz magnetic fields. New J. Phys. 18, 013045, 13 pages (2016).
Nahata, A. et al., Coherent detection of freely propagating terahertz radiation by electro-optic sampling. Appl. Phys. Lett. 68, 150-152 (1996).
Nehrkorn, J. et al., Zero-field splittings in metHb and metMb with aquo and fluoro ligands: a FD-FT THz-EPR study. Mol. Phys. 111, 2696-2707 (2013).
Osa, S. et al., A tetranuclear 3d-4f single molecule magnet: $[Cu^{II}LTb^{III}(hfac)_2]_2$. J. Am. Chem. Soc. 126(2), 420-421 (2004).
Rini, M. et al. Control of the electronic phase of a manganite by mode-selective vibrational excitation. Nature 449, 72-74 (2007).
Shalaby, M. et al., Demonstration of a low-frequency three-dimensional terahertz bullet with extreme brightness. Nature Commun. 6, 5976, 8 pages (2015).
Simon, J. et al., Single-photon bus connecting spin-wave quantum memories. Nature Phys. 3, 765-769 (2007).
Werley, C.A. et al., Pulsed laser noise analysis and pump-probe signal detection with a data acquisition card, Rev. Sci. Instrum. 82. 123108-1-6 (2011).
White, R.M. et al., Light scattering from magnetic excitations in orthoferrites. Phys. Rev. B 25, 1822-1836 (1982).
Wienholdt, S. et al., THz switching ofantiferromagnets and ferrimagnets. Phys. Rev. Lett. 108, 247207-1-5 (2012).
Woerner, M. et al., Ultrafast two-dimensional terahertz spectroscopy of elementary excitations in solids. New J. Phys. 15, 025039, 17 pages (2013).
Yamaguchi, K. et al., Coherent control of spin precession motion with impulsive magnetic fields of half-cycle terahertz radiation. Phys. Rev. Lett. 105, 237201-1-4 (2010).
Yeh, K.-L. et al., Generation of 10~ultrashort terahertz pulses by optical rectification. Appl. Phys. Lett. 90, 171121-1-3 (2007).

* cited by examiner

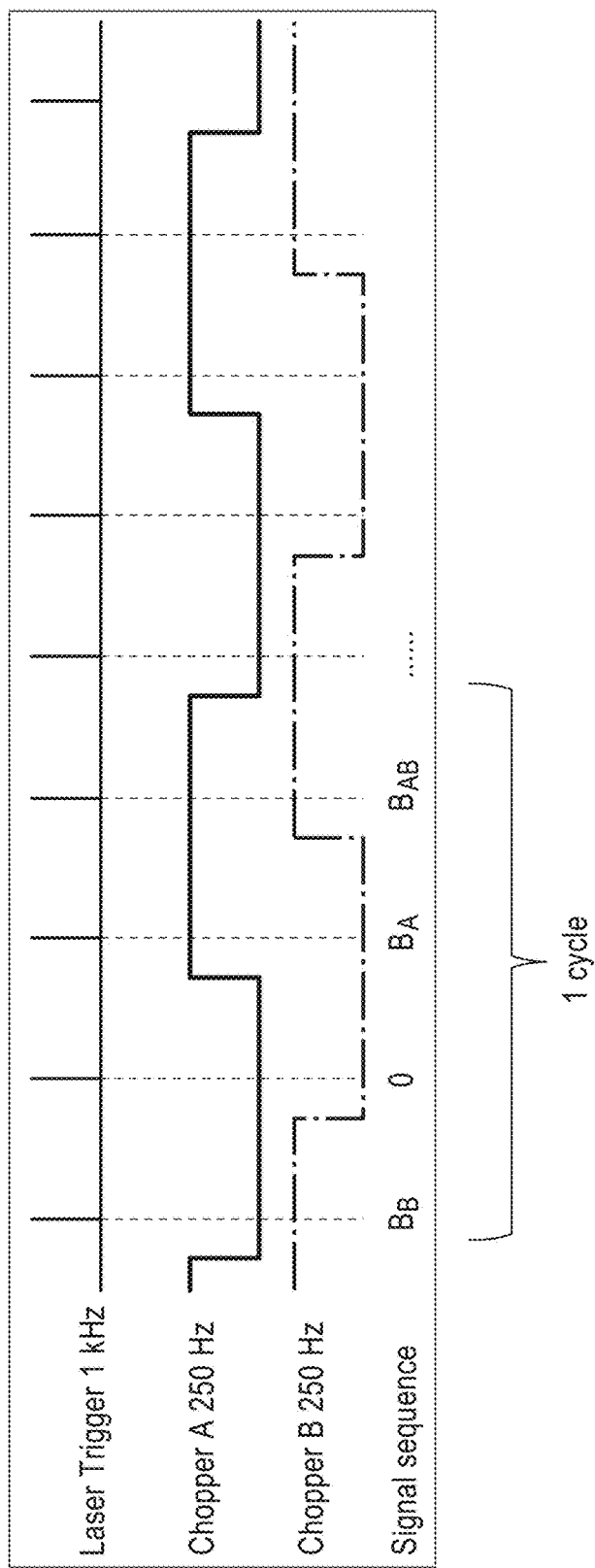

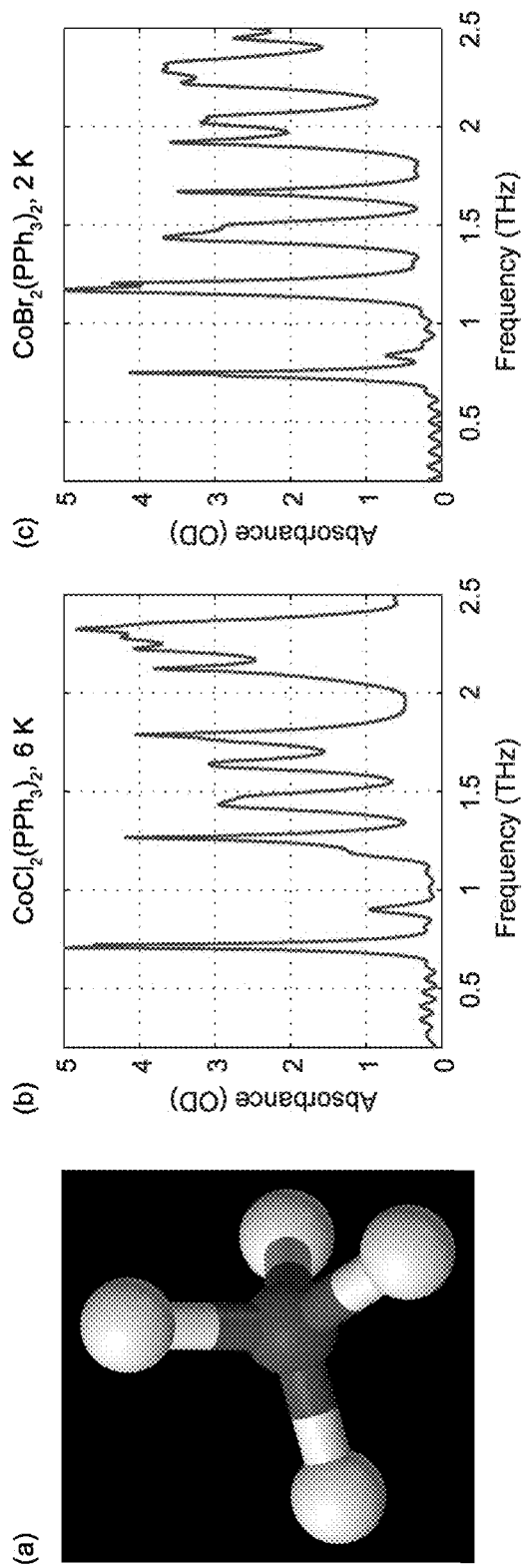

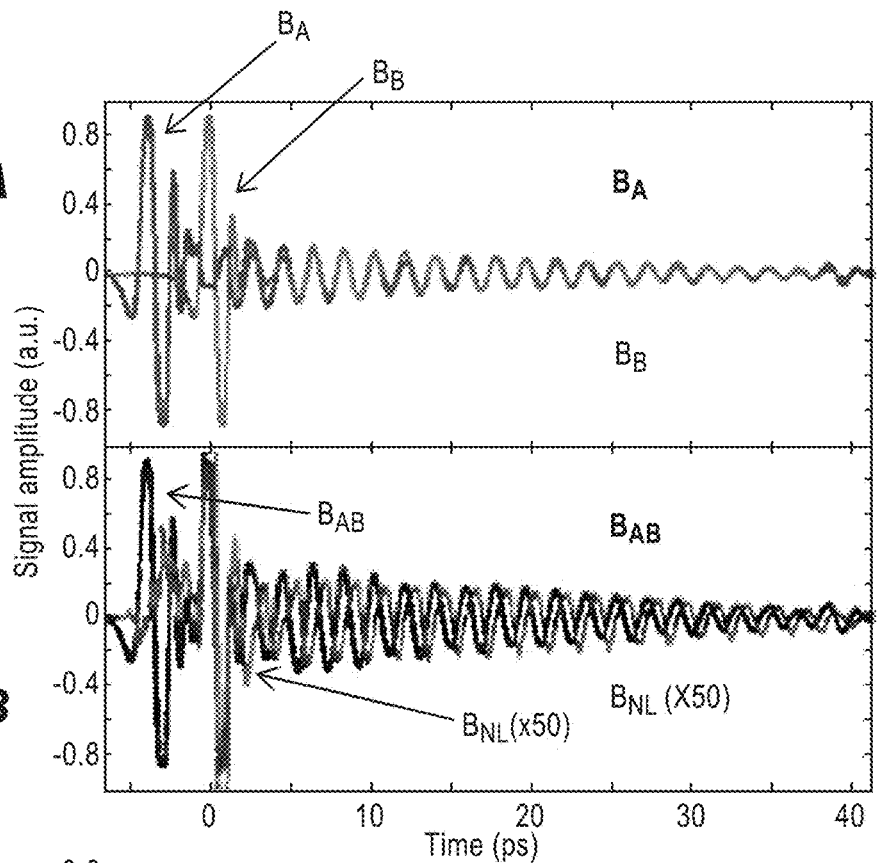
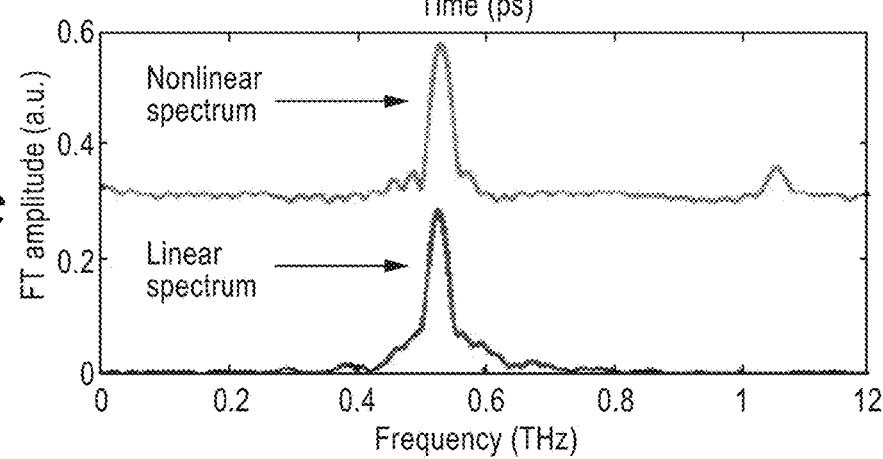

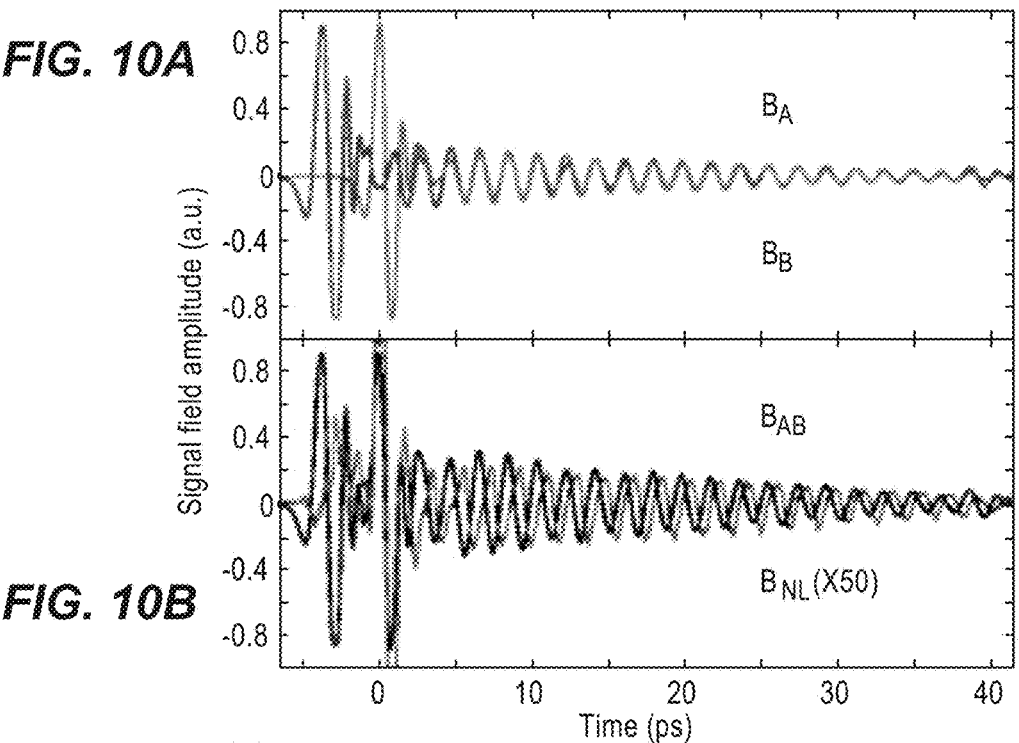
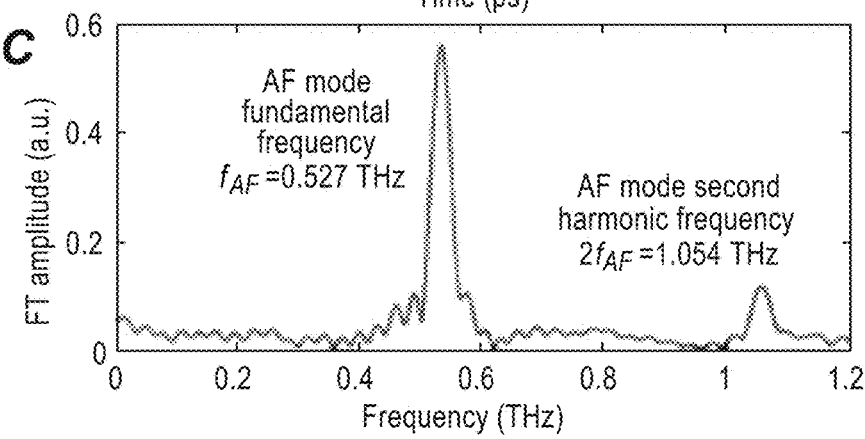
FIG. 10A
FIG. 10B
FIG. 10C

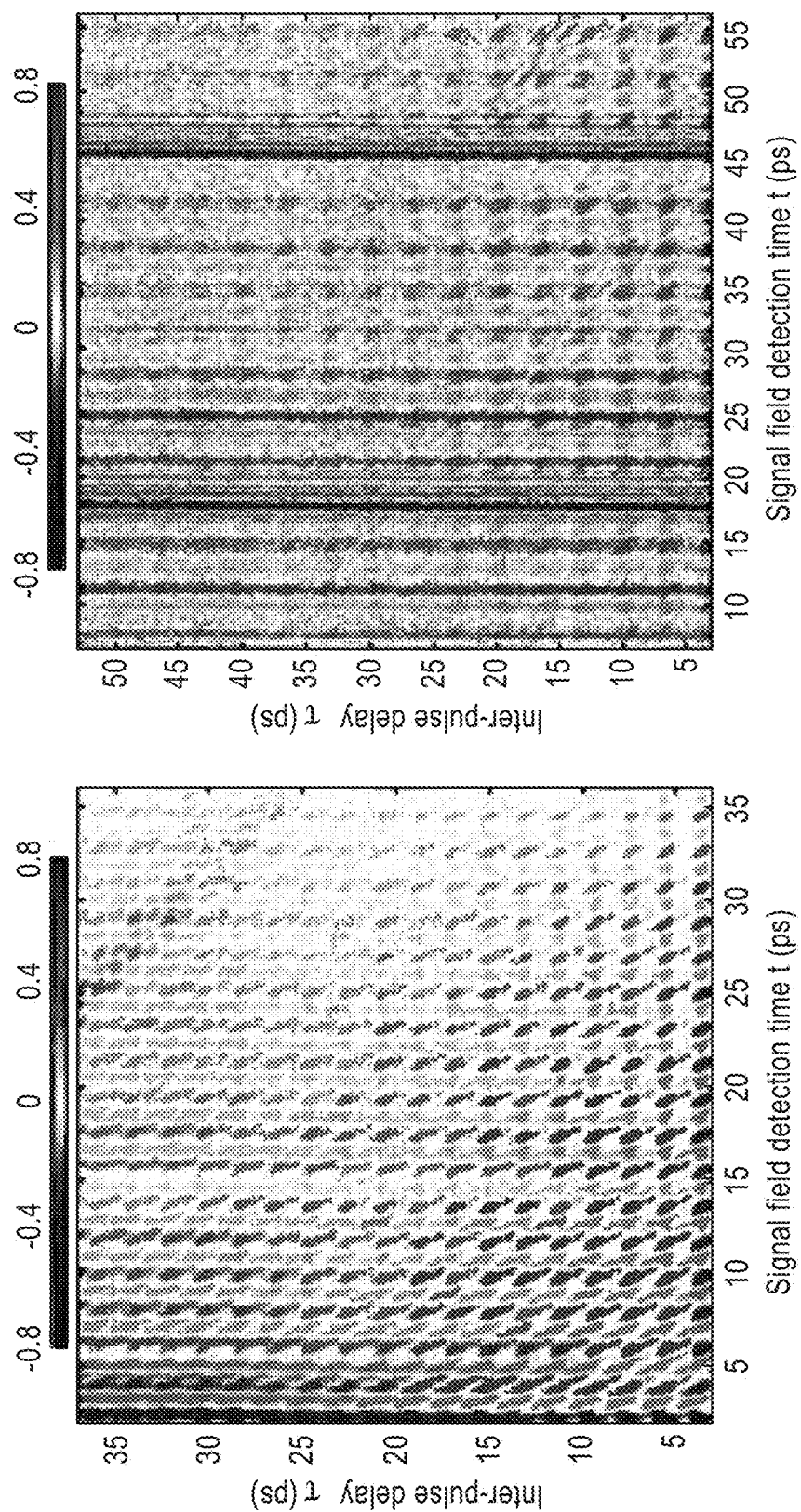

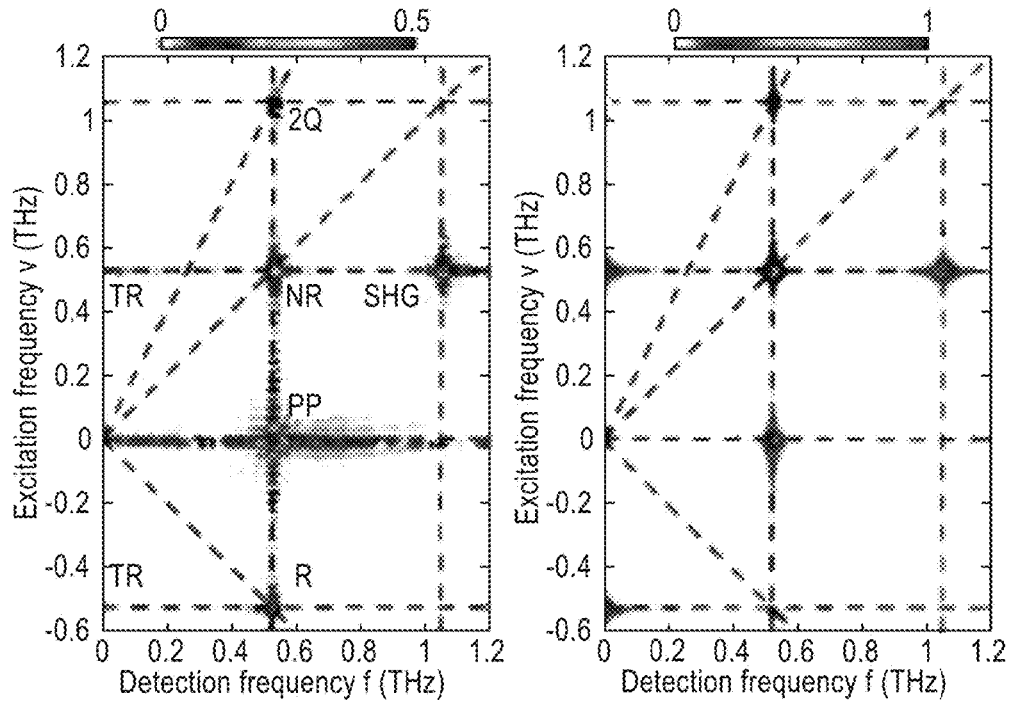
*FIG. 12A*  *FIG. 12B*
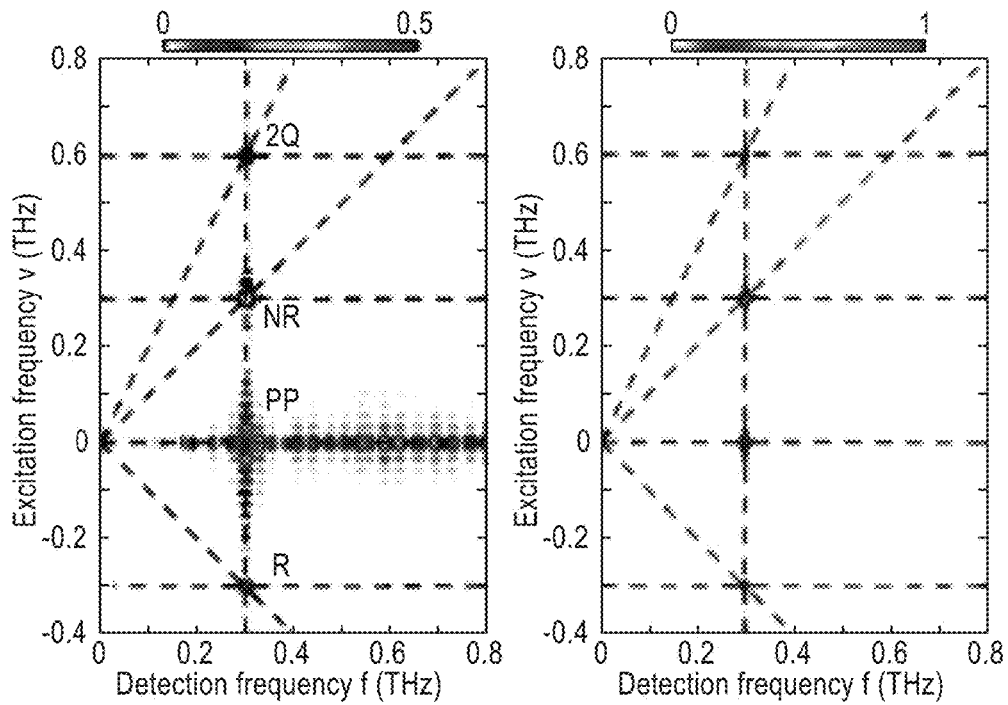
*FIG. 12C*  *FIG. 12D*

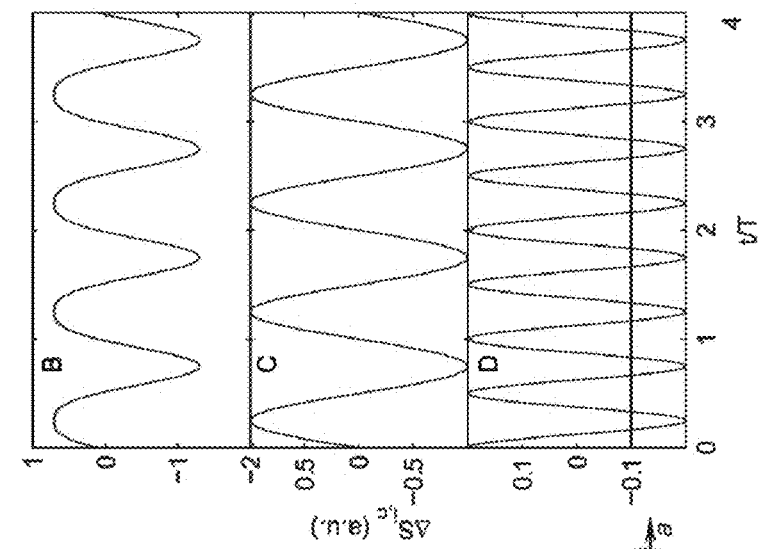
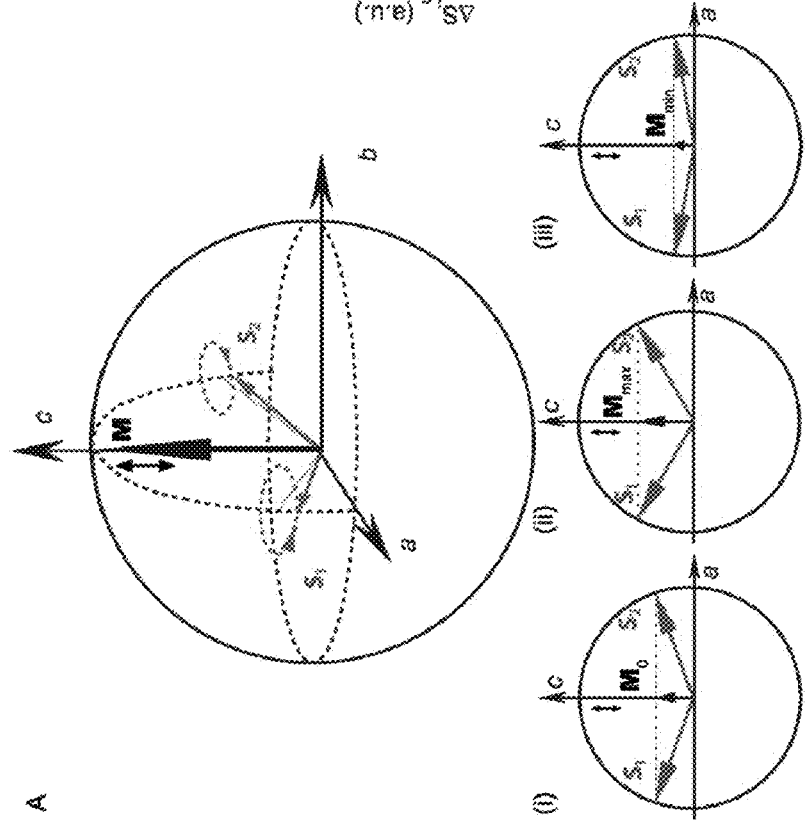
FIG. 17B
FIG. 17C
FIG. 17D
FIG. 17A

SYSTEMS, APPARATUS, AND METHODS OF NONLINEAR TERAHERTZ (THZ) MAGNETIC RESONANCE MEASUREMENT

CROSS-REFERENCES TO RELATED APPLICATIONS

This application claims priority to U.S. Application No. 62/338,843, filed May 19, 2016, entitled "NONLINEAR TERAHERTZ MAGNETIC RESONANCE MEASUREMENT OF CHEMICAL AND BIOLOGICAL MATERIALS," which is hereby incorporated herein by reference in its entirety.

GOVERNMENT SUPPORT

This invention was made with Government support under Grant No. N00014-13-1-0509 awarded by the Office of Naval Research and under Grant No. CHE-1111557 awarded by the National Science Foundation. The Government has certain rights in the invention.

BACKGROUND

The field of magnetic resonance is well established in research and commercial applications. For example, nuclear magnetic resonance (NMR) can measure the transitions between quantum-mechanical spin states of atomic nuclei, such as $^1H$, $^{13}C$, and $^{15}N$. In another example, electron spin resonance (ESR) can measure transitions between quantum-mechanical spin states of electrons. In both cases, the simplest type of measurement is linear spectroscopy, which involves measurement of a signal that is linearly proportional to the amplitude of incident electromagnetic radiation. This signal can be used to estimate the spin transition frequency. In some cases, a static or "DC" magnetic field, labeled $B_0$, can be applied, and the transition frequency is typically proportional to the magnitude of $B_0$. In addition, new transitions can be generated and the original transition peaks are split and shifted due to Zeeman interactions. The transition frequency in all cases are dependent on the magnitude of $B_0$.

Existing techniques typically measure NMR transitions having frequencies in the range of about 50 MHz to about 1000 MHz (in the radiofrequency, or RF, range). For ESR transitions, only those in the frequency range of about 5 GHz to less than 1000 GHz (in the microwave range of the spectrum) are explored.

There are also various ESR transitions in the THz regime. For example, in small molecules or large molecules including biomolecules such as proteins, some ESR transitions may be highly sensitive to molecular structure and environment including the identities and geometries of ligands of the ions in question. Thus the transitions can be used for identification of chemical species or for characterization of the ligand binding or molecular configuration around ions. They can also be used to distinguish different possible molecular configurations including those of biomolecules such as proteins. However, due to the limitations of available THz light sources, these THz ESR transitions remain largely unexplored.

SUMMARY

Embodiments of the present technology generally relate to nonlinear THz spectroscopy. In one example, an apparatus for nonlinear terahertz (THz) spectroscopy includes a THz radiation source to illuminate a sample with a plurality of THz pulses. The plurality of THz pulses includes a first copy of a first THz pulse, a first copy of a second THz pulse, and a pulse train including a second copy of the first THz pulse and a second copy of the second THz pulse separated by an inter-pulse delay $\tau$. The pulse train induces an electron spin resonance (ESR) in the sample. The apparatus also includes a detector, in optical communication with the sample, to generate a first signal $B_A$ representing a response of the sample to the first copy of the first THz pulse, a second signal $B_B$ representing a response of the sample to the first copy of the second THz pulse, and a third signal $B_{AB}$ representing a response of the sample to the pulse train. The apparatus further includes a processor, operably coupled to the detector, to estimate a nonlinear ESR response $B_{NL}$ of the sample to the pulse train based on the first signal $B_A$, the second signal $B_B$, and the third signal $B_{AB}$.

In another example, a method of nonlinear terahertz (THz) spectroscopy includes illuminating a sample with a first copy of the first THz pulse and generating a first signal $B_A$ representing a response of the sample to the first copy of the first THz pulse. The method also includes illuminating the sample with a first copy of a second THz pulse and generating a second signal $B_B$ representing a response of the sample to the first copy of the second THz pulse. The method also includes illuminating the sample with a pulse train including the a second copy of the first THz pulse and a second copy of the second THz pulse, separated by an inter-pulse delay $\tau$. The pulse train induces an electron spin resonance (ESR) in the sample. The method further includes generating a third signal $B_{AB}$ representing a response of the sample to the pulse train. The method also includes estimating a nonlinear ESR signal $B_{NL}$ based on the first signal $B_A$, the second signal $B_B$, and the third signal $B_{AB}$.

In yet another example, A system for nonlinear terahertz (THz) spectroscopy includes a THz radiation source illuminate a sample with a plurality of THz pulses. The plurality of THz pulses includes a plurality of THz pulse groups and an ith THz pulse group in the plurality of THz pulse groups includes a first copy of a first THz pulse, a first copy of a second THz pulse, and a pulse train including a second copy of the first THz pulse and a second copy of the second THz pulse separated by an inter-pulse delay $\tau_i$, where i is a positive integer. The pulse train induces an electron spin resonance (ESR) in the sample. The system also includes a detector in optical communication with the sample. For the ith THz pulse group in the plurality of THz pulse groups, the detector generates a first signal $B_A(t, \tau_i)$ representing a response of the sample to the first copy of the first THz pulse, a second signal $B_B(t, \tau_i)$ representing a response of the sample to the first copy of the second THz pulse, and a third signal $B_{AB}(t, \tau_i)$ representing a response of the sample to the pulse train. The system further includes a processor, operably coupled to the detector, to estimate a nonlinear ESR signal $B_{NL}$ for the ith THz pulse group based on the first signal $B_A(t, \tau_i)$, the second signal $B_B(t,$ and the third signal $B_{AB}(t, \tau_i)$. The processor further performs a 2D Fourier transform to the nonlinear ESR signal $B_{NL}(t, \tau_i)$ with respect to the time t and the inter-pulse delay $\tau$ so as to estimate at least one of a ZFS or a spin-spin interaction length of the sample.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 2B illustrates a differential chopping detection scheme to isolate the time-domain nonlinear signal $B_{NL}$ induced by two incident THz pulses.

FIG. 4A illustrates a molecular structure of $CoX_2(PPh_3)_2$ (X=Cl, Br) complexes.

FIGS. 4B and 4C show linear THz absorption spectra of $CoCl_2(PPh_3)_2$ and $CoBr_2(PPh_3)_2$ complexes in the absence of an external magnetic field, respectively.

FIGS. 6A-6C show time-domain nonlinear spin resonance signal extraction to measure the nonlinear spin resonance signals which can be used to estimate ZFS values from molecular complexes and proteins.

FIGS. 10A-10C illustrate nonlinear signal extraction from signals measured by the differential chopping detection method in a YFO crystal.

FIGS. 11A and 11B show normalized 2D time-time plots of $B_{NL}(\tau, t)$ from the AF mode and F mode generated in FIGS. 9A and 9B, respectively.

FIGS. 12A and 12B show experimental and simulated 2D magnitude spectra, respectively, of AF mode excited by THz pulses in YFO.

FIGS. 12C and 12D show experimental and simulated 2D magnitude spectra, respectively, F mode excited by THz pulses in YFO.

FIGS. 17A-17D illustrate temporal evolution of sub-lattice spins in AF magnon mode in YFO.

DETAILED DESCRIPTION

Overview

Figure 1:
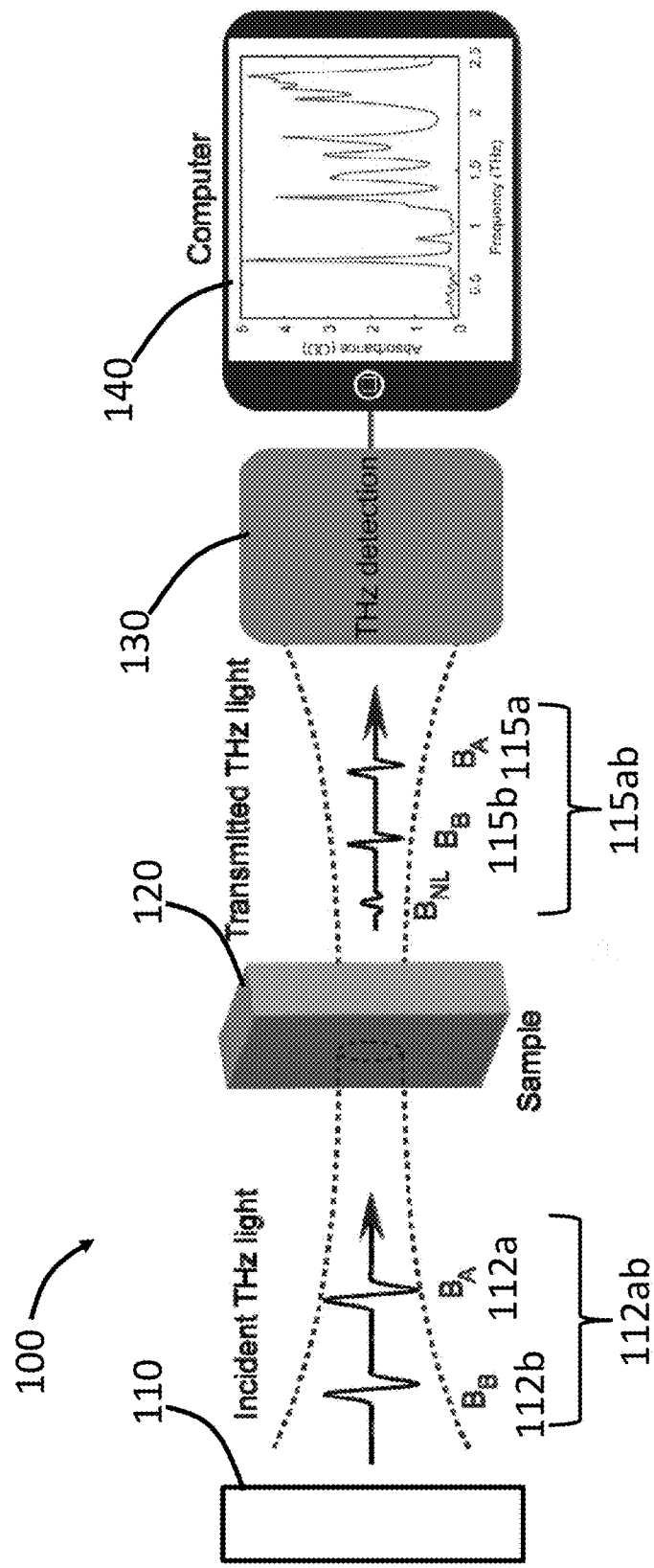
FIG. 1 shows a schematic of a system for nonlinear terahertz (THz) spectroscopy measuring electron spin resonance (ESR) in a sample.

Systems, apparatus, and methods described herein employ nonlinear terahertz (THz) spectroscopy to investigate various electron spin resonance (ESR) transitions in a sample. The acquired spectra can be used to, for example, identify the chemical and biological composition of the sample. In this technique, a sample is illuminated by two THz pulses separately, generating two signals, designated as $B_A$ and $B_B$ as a function of the detection time (real time) t, corresponding to the first and second THz pulse, respectively, after interaction with the sample. The interaction includes excitation of at least one ESR transition in the sample. The sample is also illuminated by the two THz pulses together, with an inter-pulse delay $\tau$, generating a third signal $B_{AB}$. Due to the nonlinearity of the interaction between the THz pulses and the sample, the third signal $B_{AB}$ is usually greater than the sum of the two individual signals $B_A$ and $B_B$. Therefore, a nonlinear signal $B_{NL}$ is then derived via $B_{NL}=B_{AB}-B_A-B_B$.

This nonlinear signal $B_{NL}$ can be then processed (e.g., Fourier transform) to yield complex Fourier-transform spectra as a function of the inter-pulse delay (e.g., a frequency-time data) to study the properties of the sample, by analyzing the amplitude and the phase of the complex Fourier-transform spectra as a function of the inter-pulse delay $\tau$. The frequency-time data can be further processed via a Fourier transform with respect to the inter-pulse delay to yield a 2D spectrum, where the ESR transitions induced by $B_A$ are correlated to the ESR transitions induced by $B_B$. Properties of the sample of interest, such as the homogeneous broadening, and couplings among different ESR transitions emerging due to spin-spin interactions, can be studied from the 2D spectrum.

The sample can also be illuminated by three THz pulses separately, generating three signals, designated as $B_A$, $B_B$, and $B_C$, corresponding to the first, second and third THz pulse, respectively, after interaction with the sample. The time delays between $B_A$ and $B_B$, and between $B_B$ and $B_C$ is designated as $T_1$ and $T_2$. The interaction includes the excitation of at least one ESR transition in the sample. The sample is subsequently illuminated by two pulses simultaneously, generating three signals, designated as $B_{AB}$, $B_{BC}$, and $B_{AC}$. The sample is subsequently illuminated by three pulses simultaneously, generating one signal $B_{ABC}$. A nonlinear signal $B_{NL}$ is measured via $B_{NL}=B_{ABC}-B_{AB}-B_{BC}-B_{AC}+B_A+B_B+B_C$. The nonlinear signal $B_{NL}$ is measured as a quasi-continuous function of $T_1$ and the detection time t at several value of $T_2$. The nonlinear signal $B_{NL}$ is then analyzed via a 2D Fourier transform with respect to the detection time t, and the first inter-pulse delay $T_1$, to yield a series of 2D spectra as functions of the excitation frequency $f_1$, and the detection frequency $f_3$, which are conjugate to $T_1$ and t, at each $T_2$. The properties of the sample, such as spectral diffusion and energy relaxation/transfer, can be analyzed from the spectral peaks in the 2D spectra as a function of $T_2$.

The sample can also be illuminated by N THz pulses separately with delays designated as $T_{N-1}$ N=2, 3, ..., N, between two neighboring pulse, generating N signals, designated as $B_N$, corresponding to the Nth THz pulse, respectively, after interaction with the sample. The sample is subsequently illuminated by a combination of 2, 3, 4, ..., N−1 and N of the train of pulses simultaneously, to generate signals that are in response to 2, 3, 4, ..., N−1 and N pulses. A nonlinear signal is measured such that the signal due to interactions with all the THz pulses can be separated. The signal is processed to obtain the properties of the sample.

In one example, a train of pulses composed of two or more time-delayed THz radiation, including broadband THz pulses with nearly single-cycle waveforms, or narrowband THz pulses with multi-cycle waveforms, or a combination of both which are generated using nonlinear optics in various nonlinear optical media, are used to interrogate the sample of interest. The polarizations of the THz magnetic fields can be all parallel or the polarizations of some of the THz magnetic fields can be perpendicular to those of the other THz magnetic fields. The sample can be powders of a material, a single crystal of a material, a solution of a material in a solvent, or a suspension of a material in a host solvent. The magnetic fields of the THz pulses are used to induce spin transitions in the sample of interest, both in the absence and/or as a function of an external magnetic field $B_0$. The nonlinear signals generated by the sample are incident onto a nonlinear optical crystal. A weak laser pulse is time delayed with respect to the THz pulse train and is overlapped onto the nonlinear optical crystal to detect the nonlinear signals that is generated from the sample with but not limited to a detection method based on electro-optic effects in the nonlinear optical crystal.

In another example, an apparatus includes a train of pulses composed of two or more time-delayed THz radiation is used to interrogate the sample of interest. A reference THz pulse overlaps with the nonlinear THz signal generated by the sample in time. Both of them are sent into an electronic mixing circuit device and are down converted to GHz frequencies by the electronic device. The nonlinear signal is then read out electronically, for example using a high-bandwidth photodetector and an oscilloscope or a spectrum analyzer.

In yet another example, a method of using a train of pulses composed of THz radiation, a sample in a THz cavity, either an optical pulse or a reference THz pulse for detection is disclosed. The train of THz radiation is incident into the THz cavity where the sample is placed. The THz cavity has a resonance frequency that can be tuned to the resonance frequency of the sample of interest. The interactions between the THz radiation and the sample can be enhanced by the cavity that leads to enhanced nonlinear signals. The nonlinear signals are measured using either the nonlinear optics based method or the electronics based method. In yet another example, the nonlinear response of the sample is measured by optical pulses that undergo frequency-doubling or sum-frequency generation or another nonlinear process in the sample. The signal produced by the nonlinear process could be detected in a homodyne or heterodyne manner.

FIG. 1 shows a schematic of a system 100 for nonlinear THz spectroscopy to measure ESR transitions in a sample 120. The system 100 includes a THz radiation source 110 (also referred to as a THz light source or a THz source) to provide THz pulses 112a and 112b (collectively referred to as THz pulses 112). In one example, the two THz pulses 112a and 112b can be substantially identical (e.g., having the same frequency, pulse duration, polarization, and power). In another example, the two THz pulses 112a and 112b can be different. For example, they can have different frequencies, pulse durations, polarization, and/or power.

The frequency of the THz pulses 112a and 112b can be about 0.1 THz to about 20 THz (e.g., about 0.1 THz, about 0.2 THz, about 0.5 THz, about 1 THz, about 2 THz, about 5 THz, about 10 THz, about 15 THz, or about 20 THz, including any values and sub ranges in between). In one example, the THz radiation source 110 delivers THz pulses 112 that are broadband. In another example, THz radiation source 110 delivers narrowband THz pulses 112.

The THz radiation source 110 can deliver the two pulses 112a and 112b separately (i.e., in a single-pulse mode). The THz radiation source 110 can also deliver the two pulses 112a and 112b together, in which case the two THz pulses 112a and 112b for a pulse train 112ab. In the pulse train 112ab, the time delay between the two THz pulses 112a and 112b is designated as τ, which is adjustable. The THz radiation source 110 can deliver a train of N pulses separately. The THz radiation source 110 can also deliver a combination of two, three, ..., N pulses out of the pulse train. The time delays between adjacent THz pulse pairs are designated as $T_{N-1}$, which are adjustable.

The THz pulses 112 delivered by the THz radiation source 110 are focused to a sample 120. The focusing can be achieved by, for example, a parabolic mirror. A detector 130 is used in the system 100 to detect the THz pulses 112 and generate signals $B_A$ 115a, $B_B$ 115b, and $B_{AB}$ 115ab, corresponding to incident THz pulses 112a, 112b, and 112ab, respectively. Typically, the signals 115a, 115bn, and 115ab are collected in the time domain, i.e., $B_A=B_A(t)$, $B_B=B_B(t)$, $B_{AB}=B_{AB}(t)$, where t is time. The system 100 can also detect the THz pulses 112 without the sample 120 and the generated signals $B_{BKGD}$ can be used as a background signal (also referred to as background noise signal). The signals $B_A$, $B_B$, and $B_{AB}$ represent the response of the sample 120 to the incident THz pulses. In some cases, these signals can be radiated from the sample 120.

The generated signals 115a, 115b, and 115ab are transmitted to a processor 140 (or a computer including a processor), which then estimates the nonlinear signal $B_{NL}$ via $B_{NL}=B_{AB}-B_A-B_B$. The processor 140 is also configured to carry out further processing, such as Fourier transform with respect to time and/or the inter-pulse delay τ (see more details below).

The system 100 can investigate various types of samples 120. For example, the sample 120 can include one or multiple single crystals. In another example, the sample 120 can include powders. In yet another example, the sample 120 can include a solution. In yet another example, the sample 120 can include a compressed pellet. In yet another example, the sample 120 can include a suspension.

The sample 120 can also include, for example, a specimen from human blood or part of a live human body, such as a human ear or finger. In this case, the system 100 can be configured to perform non-contact analysis of the sample 120. In addition, the detector 130 can collect reflected or diffused THz pulses to generate the signals 115a, 115b, and 115c (instead of collecting transmitted THz pulses).

A direct current (DC) magnetic field can be applied to the sample 120 to induce spectral shifts and Zeeman splitting. This can help separate possible overlap of certain spin transitions (e.g., due to degeneracy). In addition, the dependence of the ESR transition frequencies as a function of magnetic field can also be determined. This dependence can also be used for identifying the chemical and/or biological compositions of the sample 120.

FIG. 1 shows two THz pulses 112a and 112b for nonlinear THz spectroscopy. In practice, any other number of THz pulses can be used. For example, the THz radiation source 110 can deliver N THz pulses separately and also deliver a pulse train including the N THz pulses, where an ith and (i+1)th THz pulse in the train is separated by a time delay $\tau_i$, i=0, 1, 2, . . . , N−1

Two-Dimension (2D) THZ Magnetic Resonance Spectroscopy

Figure 2A:
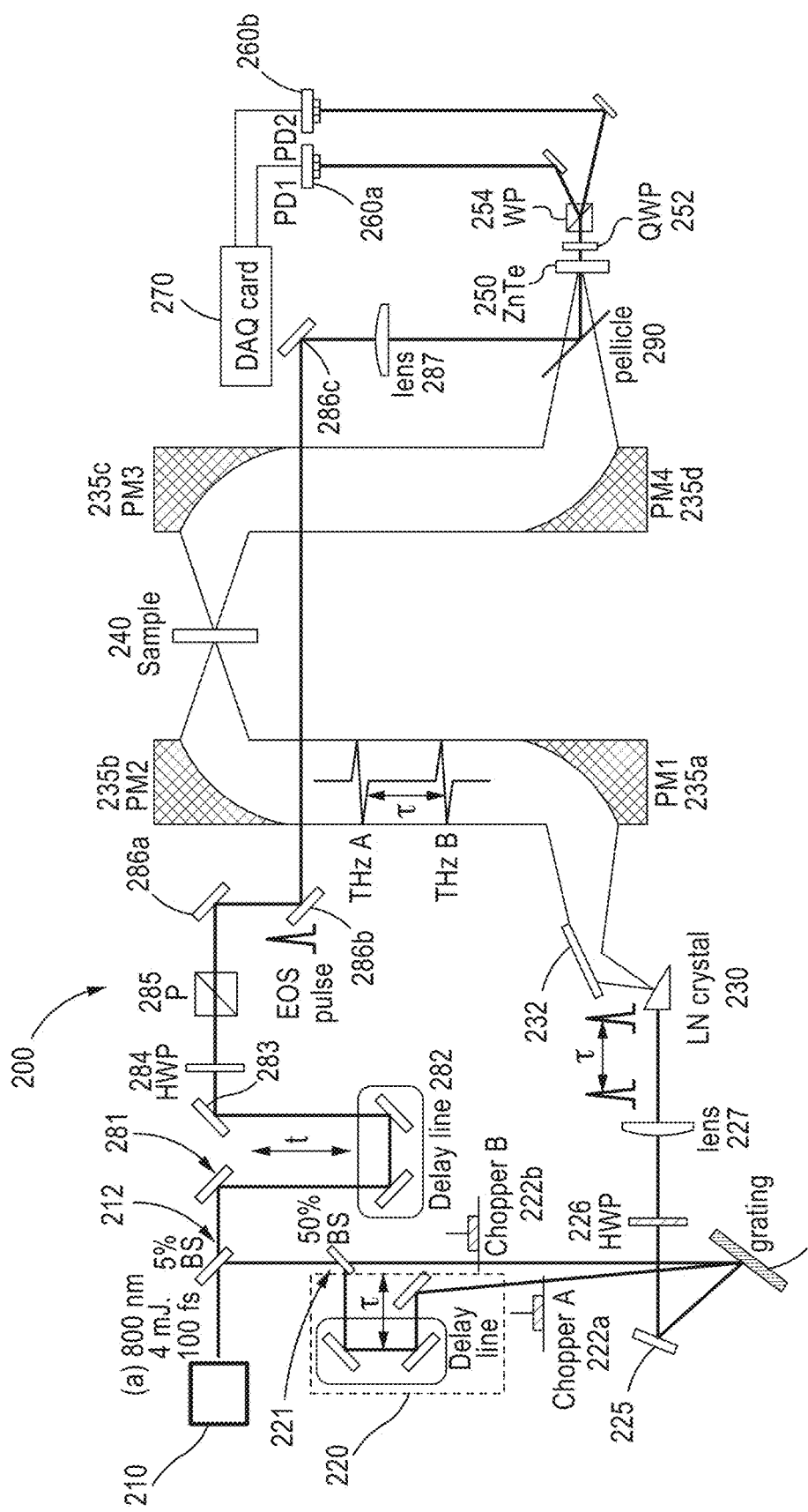
FIG. 2A shows a system for two-dimensional (2D) THz magnetic resonance spectroscopy using nonlinear optical rectification for THz generation and electro-optic sampling for THz detection.

FIG. 2A shows a system 200 for two-dimensional (2D) THz magnetic resonance spectroscopy implemented via nonlinear optics method. In this 2D spectroscopy, the acquired signal B is a function of both time t and the inter-pulse delay $\tau$, i.e., $B=B(t, \tau)$. In this case, a 2D Fourier transform can be performed on the acquired signal B, with respect to t and $\tau$, so as to generate a 2D spectrum $S(f, v)$, where the variable f may give frequencies in the signal field and the variable v may give frequencies that the sample responds to in the sequence of applied THz pulses (see, e.g., FIG. 7 and FIG. 13A).

The system 200 includes a laser 210 to provide optical pulses. The optical pulses can be in the near infrared regimes (e.g., about 800 nm to about 1800 nm, including any values and sub ranges in between) and have an ultrashort pulse duration (e.g., about 100 fs). The repetition rate of the laser 210 can be on the order of kHz (e.g., about 1 kHz). The optical pulses provided by the laser 210 is split by a beam splitter 212 into two parts. The first part (reflected part in FIG. 2A) has a majority of the pulse energy (e.g., greater than 80%, greater than 85%, greater than 90%, or greater than 95%, including any values and sub ranges in between) and is employed to generate THz pulses via nonlinear optics. The second part (transmitted part in FIG. 2A) is employed for THz detection.

The optical pulses reflected by the beam splitter 212 is transmitted to another beam splitter 221, which can be a 50:50 beam splitter to divide the optical pulses into two equal portions. One portion is sent to a delay stage 220 before arriving at a grating 224, while the other portion propagates directly to the grating 224, where the two portions are combined.

The delay stage 220 is used to generate the inter-pulse delay $\tau$ and can change the inter-pulse delay $\tau$. In some cases, the inter-pulse delay $\tau$ can be adjusted between about 0 ps and about 100 ps. The step size of the adjustment can depend on the precision of the translation of the delay stage 220. For example, the delay stage 200 can use a micrometer positioning stage to move the reflectors. In this case, the step size of the delay created by moving the positioning stage can be on the order of a few fs (e.g., about 3 fs, about 5 fs, about 10 fs, or about 20 fs, including any values and sub ranges in between). In practice, other step sizes can also be used, such as on the order of ps (e.g., about 1 ps, about 2 ps, or about 5 ps, including any values and sub ranges in between).

The two optical pulses combined at the grating 224 are reflected by a reflector 225, transmitted through a half wave plate 226, and focused by a lens 227, before being transmitted through a nonlinear crystal 230 to generate THz pulses via optical rectification. In some cases, the nonlinear crystal 230 can include a lithium niobate (LN) crystal. In yet other cases, the nonlinear crystal 230 can include a gallium selenide (GaSe) crystal. In yet other cases, the nonlinear crystal 230 can include organic nonlinear optical crystals such as OH1 (2-(3-(4-Hydroxystyryl)-5,5-dimethylcyclohex-2-enylidene)malononitrile) and DSTMS (4-N,N-dimethylamino-4'-N'-methyl-stilbazolium 2,4,6-trimethylbenzenesulfonate). Each optical pulse can generate a corresponding THz pulse and the resulting THz pulses are designated as $B_A$ (created by the first optical pulse), $B_B$ (created by the second optical pulse), and $B_{AB}$ (created by the pulse train including both optical pulses). The THz pulses generated via optical rectification of fs optical pulses are usually also ultrashort pulses with broad spectral bandwidth typically spanning some part of the frequency range from about 100 GHz to about 20 THz (including any values and sub ranges in between). More details of optical rectification can be found in U.S. Pat. No. 7,894,126 B2, entitled "Broadband terahertz radiation generation and detection system and method," which is hereby incorporated herein by reference in its entirety.

The THz pulses after the nonlinear crystal 230 are collimated by a first parabolic mirror 235a (e.g., an off-axis parabolic mirror) and then focused by a second parabolic mirror 235b onto a sample 240. After interacting with the sample 240, the THz pulses are refocused by two parabolic mirrors 235c and 235d into an electro-optical (EO) crystal 250 for detection. In some cases, the EO crystal 250 can include a ZnTe crystal. In yet other cases, the EO crystal 250 can include a GaP crystal. In yet other cases, the EO crystal 250 can include a GaSe crystal.

At the same time, an optical pulse, transmitted by the beam splitter 212, is also guided to the EO crystal 250 for THz detection. The optical pulse is also referred to as a probe pulse, a gate pulse, or a read-out pulse. In the system 200, the probe pulse is reflected by a reflector 281 into a delay stage 282, which can generate a time delay t with respect to the second THz pulse B. The probe pulse after the delay stage 282 is then reflected by a reflector 283, transmitted through a half wave plate 284, a polarizer 285, before being reflected by a series of reflectors 286a, 286b, and 286c toward a pellicle 290. A lens 287 can also be inserted into the beam path of the probe beam to modify the divergence of the probe pulse. The pellicle 290 functions as a beam combiner to combine the THz pulses and the probe pulse.

The detection of the THz pulses is based on electro-optic (EO) sampling. The THz pulses are overlapped with the time-delayed probe pulse in the EO crystal 250. The probe pulse experiences transient birefringence induced by THz electric field in the EO crystal 250 and THz electric field amplitude is read out by birefringence optics. Varying the time delay between the THz pulses and the probe pulse can then map out the temporal waveform of the THz pulses.

The probe pulse after transmitting through the EO crystal 250 propagates through a quarter wave plate 252 and a Wollaston prism 254 that splits the probe pulse into two portions, each of which has a distinct polarization state. Two optical detector 260a and 260b are used to collect the two portions of the probe pulses and the generated data is sent to a data acquisition (DAQ) card 270 for further processing (e.g., Fourier transform).

The THz detection can be achieved by other methods as well. For example, it is also possible to detect the sample nonlinear response through a linear and/or a nonlinear optical process either by time-resolved method or frequency-resolved method. In this case, the optical pulse is directed into the sample directly. Possible linear optical processes include reflectivity, birefringence, absorption, scattering etc., of a fs optical pulse at any wavelength (from infrared to x-rays). Nonlinear optical processes may include frequency shift (Stark effect), frequency-doubling (second-harmonic generation in either homodyne or heterodyne mode), sum-frequency generation (in either homodyne or heterodyne mode), etc., of a fs optical pulse at any wavelength.

In FIG. 2A, two optical choppers 222a and 222b are placed within the beam paths of the two optical pulses that are used for THz generation. FIG. 2B illustrates a differential chopping detection scheme to isolate the time-domain nonlinear signal $B_{NL}$ induced by the two incident THz pulses A and B described above. In this scheme, the laser 210 has a repetition rate of 1 kHz, and the two optical choppers have a modulation frequency at 250 Hz (i.e., transmit 250 optical pulses every second). In this case, the probe pulse has the original repetition rate of 1 kHz and the THz pulses have a repetition rate of 250 Hz. As shown in FIG. 2B, the opening times of the two choppers 222a and 22b are offset by about a quarter of the modulation frequency (e.g., about 1 ms). In four successive laser shots in one cycle, the first shot measures $B_B$, the second shot measures background noise, the third shot measures $B_A$, and the last shot measures $B_{AB}$.

In addition to the nonlinear optics approach described above, electronics methods can also be employed to generate and/or detect the THz pulses. In this method, THz fields can be generated by frequency-doubling of sub-THz microwave fields from microwave oscillators. As a result, the generated THz field may contain a narrow frequency bandwidth and have a tunable central frequency. For detection, a THz field at a nearby frequency can be generated and mixed with the THz signal fields in an electronic mixer so as to down-convert the signals to GHz (microwave) frequencies. The down-converted signals are then read out via a spectrum analyzer or digitizing oscilloscope. The signal to noise ratio and data acquisition time in this approach can be favorable, particularly if the spin transition frequencies of interest are known in advance. In some cases, the system 200 can use both nonlinear optics approach and the electronics approach for THz generation and/or detection.

Various methods can be implemented by the systems described above. In one example, a sequence of THz pulses can be applied to a sample (e.g., 120 or 240) to elicit a nonlinear spin signal that is coherently radiated by the sample. For example, a sequence of just two pulses can be applied and the resulting nonlinear signal can be measured. The inter-pulse delay between the two pulses and the relative phases between specified frequency components of the two pulses can be controlled and varied. A nonlinear signal $B_{NL}$ can be measured as a function of the inter-pulse delay and/or the relative phase.

The nonlinear signal $B_{NL}$ is a coherent electromagnetic field and is usually similar in character to the fields that induced it (i.e., the incident THz field). The time-dependent profile of the nonlinear signal field S(t) can be measured in the systems above. In many cases S(t) measured as a function of a time variable such as the time delay τ between two applied pulses or two user-defined waveforms, and the signal field S(τ, t) is therefore a function of two time variables. The signal field is generally a vector with well-defined polarization properties. For simplicity it can be written as a scalar, but in some measurements the polarization properties of the incident fields and the measured signal field may be specified and the vector nature of the fields may be exploited to extract additional information about the sample.

A commonly measured signal of this type is called a "spin echo," in which the signal peak emerges after a delay time τ equal to the time delay between two applied pulses, reminiscent of an audible echo that is heard some time after the original sound is produced.

In many cases it can be convenient to present the ESR data as functions of frequency rather than time variables. This can be achieved through Fourier transformation of the time-variant signal S(τ, t). The signal after Fourier transformation can be written as S(v, f), where the variable f is the frequency in the signal field and the variable v is the frequency that the sample responds to in the sequence of applied pulses. As described above, this type of measurement is generally referred to as "two-dimensional (2D) spectroscopy" and the signal is typically written as a function of two frequency variables.

There can be several variations on the 2D spectroscopy method described above. For example, more than two variables can be used to write time-variant signal so as to perform 3D or generally multidimensional spectroscopy. In another example, the extent of the temporal ranges, the time resolution, the frequency components, the light polarizations, and other features may be tuned to optimize the measurement. In addition, complex waveforms with many pulses may be used.

In practical implementation of the systems 100 and 200, a database of magnetic resonance spectral information can be established and then used for optimizing the measurement of a particular sample. The optimization can include, for example, selection of the mode of nonlinear measurements (e.g., 1D spectroscopy, 2D spectroscopy, spin echo, or other modes), tailoring of the applied THz fields (e.g., spectral regime of the THz pulses, bandwidth of the THz pulses, and polarizations), and the detection method (EO sampling or electronic down-conversion). The optimization can also include the decision of whether to apply an external magnetic field. If the data are not already available for a sample, one can first use a broadband THz source and detection method to locate the spin transition frequencies of interest. One can also apply a magnetic field to differentiate transitions of magnetic origin from those of non-magnetic origin And based on the results one can decide upon the optimal measurements and configurations.

Linear Measurement of Zero-Field Splitting (ZFS) and Spin-Spin Interaction

The systems described above (e.g., systems 100 and 200) can be used to estimate the zero-field splitting (ZFS) values and spin-spin interaction values of the sample. In these cases, the sample can include transition metal (TM) ions and/or rare earth (RE) ions. The ions may be contained in small molecules or very large molecules including proteins and other biomolecular species. The systems therefore can be used for characterization of molecules and biomolecules with possible applications in distinguishing certain molecular forms such as protein species.

The ZFS value refers to spin transition frequencies in the absence of any externally applied magnetic field (i.e. $B_0$=0). The spin-spin interaction strengths (also referred to as "couplings") describes the extent to which spins on nearby electrons (typically spins of electrons on nearby ions) interact with each other or the extent to which spins on electrons and nuclei interact with each other.

The ZFS and coupling values can be highly sensitive to molecular structure and environment including the identities and geometries of ligands of the ions in question. Thus the values can be used for identification of chemical species or for characterization of the ligand binding or molecular configuration around ions. They may also be used to distinguish different possible molecular configurations including those of biomolecules such as proteins. A particular possibility of interest would be distinction between different forms of biomolecules related to human health, such as normal and glycated hemoglobin that are of interest to patients suffering from diabetes.

The systems described above can measure molecular spin signals in the THz frequency range (e.g., about 0.1 THz to about 20 THz) of high-spin TM and RE ions present in molecular complexes and/or biomolecules such as proteins. Nonlinear THz ESR signals, including 2D THz ESR signals, allow the extraction of ZFS and coupling values even when the linear spin transitions are buried underneath congested absorption features, such as those of large molecules or biomolecules. Since THz light can penetrate human skin, the technology can also permit noninvasive diagnosis of pathological changes of proteins and other constituents in human blood, muscles, and tissue.

Molecular complexes including TM and/or RE ions with valence electrons in coordination with ligands assume well defined geometries with known symmetries, and may undergo structural distortions into configurations with reduced symmetries, depending on the interactions between the central ion and each ligand. Consequently, the quantum-mechanical orbitals of the valence electrons undergo shifts in their energies, usually referred to as crystal field splitting, and the valence electron spins arrange to form an energetically stable ground state. In many molecular complexes, the central TM or RE ions are found in a high-spin configuration, i.e. unpaired electron spins are all parallel, in the ground state. The total spin angular momentum is given by a quantum number "S." In this case the electron spin sublevels (labeled by quantum number ms) can have different energies. The differences between the electron spin energy levels are the ZFSs.

Figures 3A, 3B:
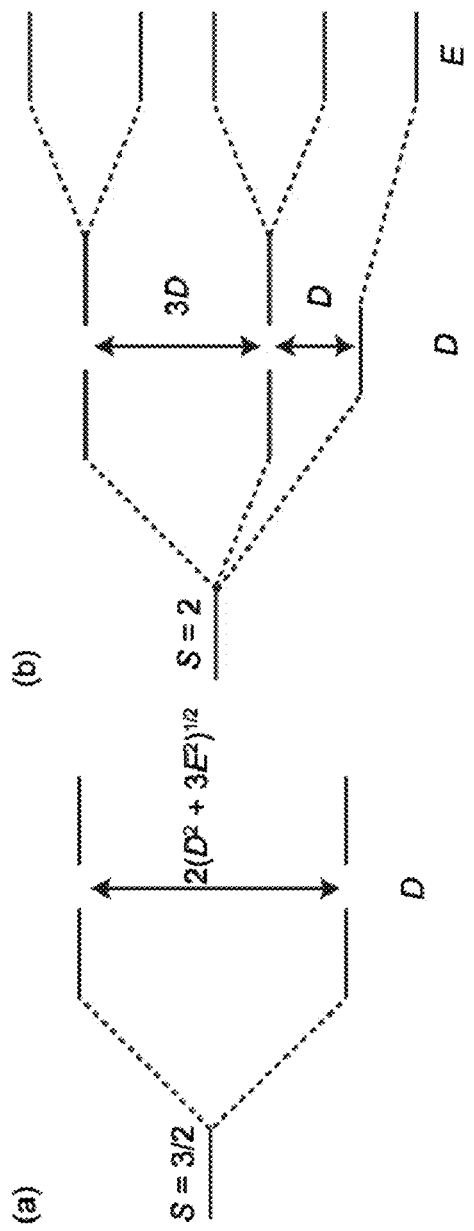
FIGS. 3A and 3B show zero-field splitting (ZFS) patterns of two spin systems with different numbers of unpaired spins.

FIGS. 3A and 3B show ZFS patterns of two spin systems with different numbers of unpaired spins. FIG. 3A shows the ZFS pattern in a high-spin Co(II) system (S=3/2), in which four degenerate spin levels split into two sets of degenerate sublevels separated by $2(D^2+3E^2)^{1/2}$. FIG. 3B shows the ZFS pattern in a high-spin Fe(II) system (S=2), where five degenerate spin levels split into three sets of sublevels under axial ZFS and further split into five sublevels under transverse ZFS.

TM and RE ions with different numbers of valence electrons can exhibit distinct ZFSs. As shown in FIG. 3A, under axial distortion away from higher symmetry such as that of a tetrahedral complex, the fourfold degenerate electron spin levels are split into two sets of twofold degenerate levels separated by $-2(D^2+3E^2)^{1/2}$, with D and E being the axial and transverse ZFS parameters respectively. The new electron spin energy levels are differentiated by their spin angular momentum quantum numbers. The ZFS of a high-spin Fe(II) ion is shown in FIG. 3B. Under axial distortion away from higher symmetry such as that of an octahedral complex, the degenerate spin energy levels split into three sets of spin sublevels, separated by D and 3D. Under rhombic distortion, the degeneracy is lifted by further splitting, which is captured by the transverse ZFS parameter E.

With the same central TM ion, complexes in coordination with different ligands can exhibit differences in their ZFS parameters, due to the subtle differences in the geometric distortion and/or charge distribution of the complex. For example, the combination of the ZFS parameters $(D^2+3E^2)^{1/2}$ in $CoCl_2(PPh_3)_2$ is about 15.0 cm' (0.45 THz) at a temperature of 6 K, while the combination of the ZFS parameters $2(D^2+3E^2)^{1/2}$ in $CoBr_2(PPh_3)_2$ is about 14.0 cm' (0.42 THz) at a temperature of 2 K. ZFS values therefore can provide exquisite sensitivity to both the composite ions and the structures of molecular complexes.

Figures 5A, 5B:
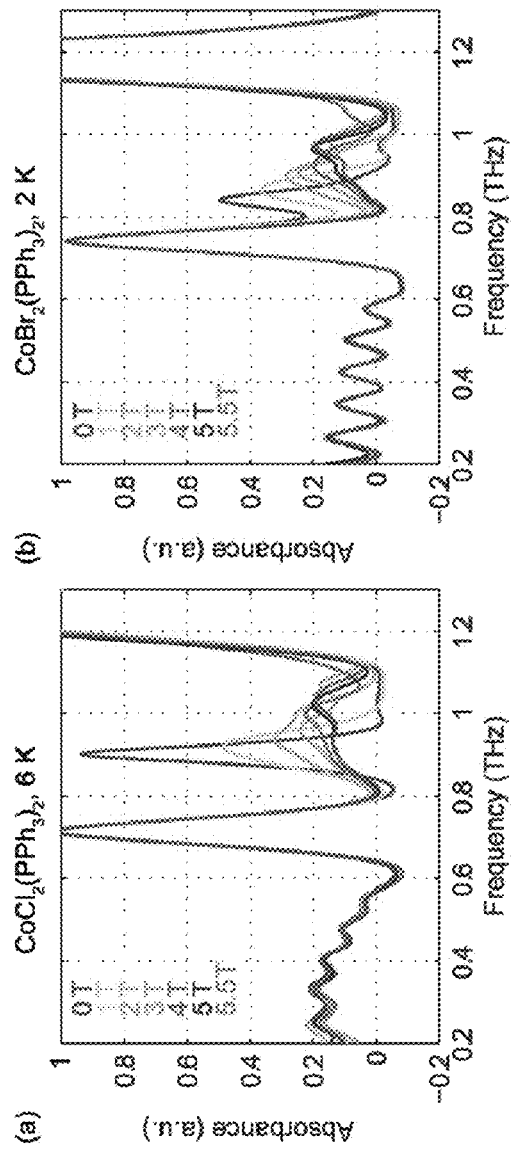
FIGS. 5A and 5B show linear THz absorption spectra of $CoCl_2(PPh_3)_2$ and $CoBr_2(PPh_3)_2$ complexes as a function of an external magnetic field.

Under an external magnetic field, the spin sublevels can undergo additional spectral shifts and splitting, due to Zeeman interactions. For example, as shown in FIGS. 5A and 5B, the spectra of $CoX_2(PPh_3)_2$ (X=Cl, Br) complexes are measured as a function of an external magnetic field at 0, 1, 2, 3, 4, 5 and 5.5 T. The peak at 0 T become broader because the degenerate spin transitions contributing to the peak become nondegenerate under the external magnetic field. By measuring the spectra as a function of the magnetic field, additional information such as the g-factor can be obtained from the amount of frequency shift. Accordingly, application of an external magnetic field $B_0$ can provide an additional experimental degree of freedom for determination of ZFS values, for determination of the g-factor and for distinction among different complexes.

In small molecules, linear THz spectroscopy measurements are often sufficient to measure ZFSs. $CoX_2(PPh_3)_2$ (X=Cl, Br) complexes are used here for illustration, but other complexes can also be investigated using the techniques described herein.

FIG. 4A illustrates a molecular structure of $CoX_2(PPh_3)_2$ (X=Cl, Br) complexes. FIGS. 4B and 4C show linear THz absorption spectra of $CoCl_2(PPh_3)_2$ and $CoBr_2(PPh_3)_2$ complexes, respectively. In $CoX_2(PPh_3)_2$ (X=Cl, Br), central Co(II) ion (central sphere) is in tetrahedral coordination with the four ligands (side spheres). In $CoCl_2(PPh_3)_2$ the linear THz absorption spectra show magnetic resonance peaks at about 0.901 THz at 6 K, corresponding to $(D^2+3E^2)^{1/2}=15.0$ cm$^{-1}$. Substituting the two $Cl^{-1}$ ligands with $Br^{-1}$, the magnetic resonance peaks change to about 0.838 THz at 2 K, corresponding to $(D^2+3E^2)^{1/2}=14.0$ cm$^{-1}$, respectively. The linear magnetic resonance spectra therefore provide sensitivity to ZFSs under different conditions.

In these measurements, a short (single-cycle) THz pulse was incident on the sample, and the transmitted signal included the short pulse followed by a much longer-duration signal (a "free-induction decay" or FID) that showed distinct oscillations at the electron spin transition frequency. Fourier transformation of the time-dependent signals from two different molecular complexes revealed the linear absorption spectra shown in FIGS. 4B and 4C, from which the ZFS values can be determined. The complexes can be distinguished easily by their different absorption spectra and ZFS values.

Nonlinear THz Spectroscopy to Measure ZFS and Spin-Spin Interaction

In simple molecules like those illustrated in FIG. 4A, the ZFS values can be measured in linear spectroscopy because they may be separated from strong competing absorption features. In large molecules such as proteins, however, the linear spectra are often dominated by broad absorption features due to low-frequency motions of polar segments. These strong features can obscure ESR absorption lines.

Figure 5C:
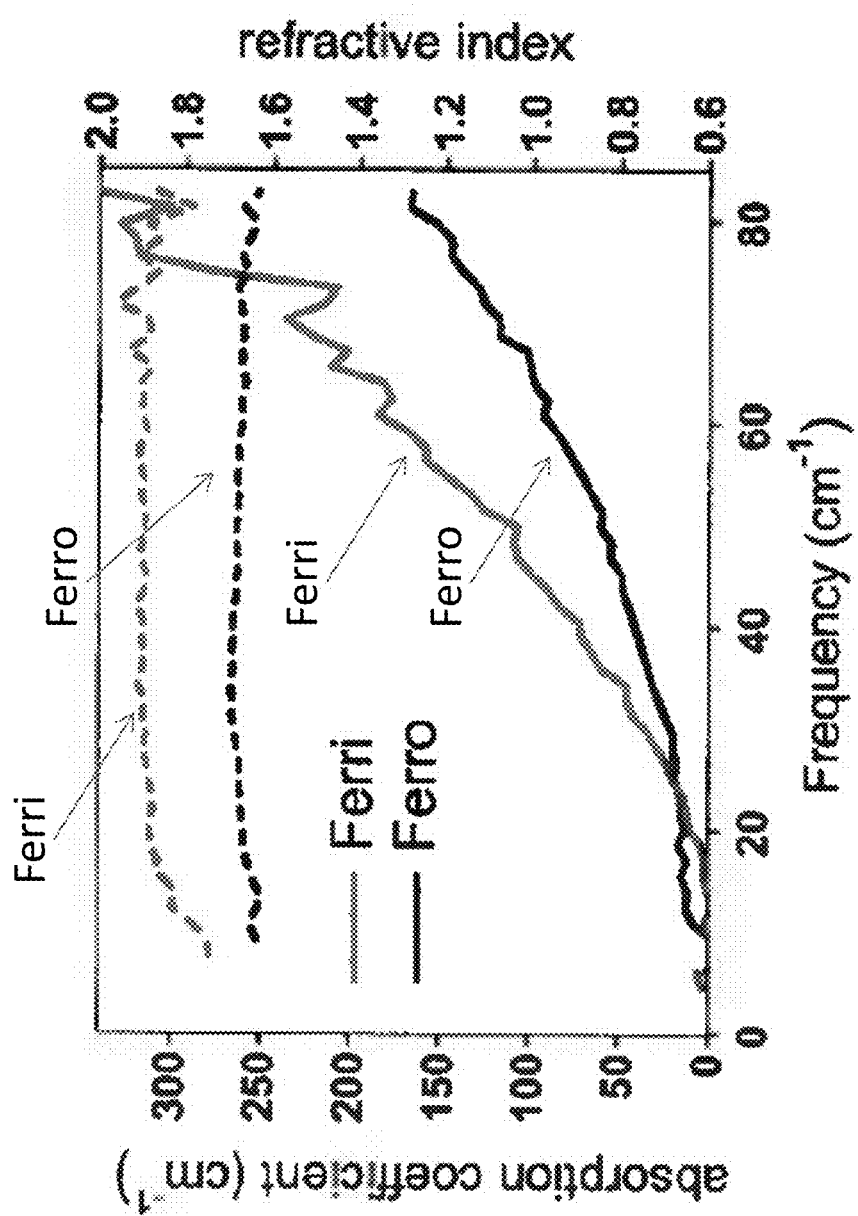
FIG. 5C shows linear THz absorption spectra of a large molecule Cytochrome complex (CytC).

FIGS. 5A and 5B show linear THz absorption spectra of $CoCl_2(PPh_3)_2$ and $CoBr_2(PPh_3)_2$ complexes as a function of an external magnetic field. FIG. 5C shows linear THz absorption spectra of a large molecule Cytochrome complex (CytC), which is a protein containing Fe ions. The solid lines are THz linear absorption spectra of films at 4% hydration of ferri-CytC containing high-spin Fe(II) ions and ferro-CytC containing low-spin Fe(III) ions. The dashed lines show the refractive index. There is no hint of an ESR transition even though the protein contains a high-spin TM ion Fe(II). The ESR absorption would be weaker and narrower than the broad spectrum shown. It would be narrower because when spin resonances are driven by a resonant field, the spins can oscillate for many cycles (i.e., they undergo slow damping or dephasing). In contrast, low frequency molecular vibrations undergo fast damping and dephasing, so they have broad absorption features. They also have stronger absorption strengths in many cases. This can hinder the application of linear THz spectroscopy for characterization of ZFS values or other spin transitions in biological samples including diagnosis of pathological changes in humans.

For large molecules, such as the CytC protein, two time-delayed THz pulses can be used to measure nonlinear spin echo signals. Spin echo signals can typically persist for much longer inter-pulse delay time τ than photon echo signals from vibrational modes, due to the much slower dephasing of the spin coherence. Therefore, after sufficient inter-pulse time delay τ, only the nonlinear echo signal may still persist. Fourier transformation of the signal may reveal the ZFS values, even though the linear spectrum does not permit the spin transition or the ZFS value to be measured. The spin echo can be measured either as a one-dimensional (1D) measurement or as a 2D measurement of the full signal field S(τ, t).

FIGS. 6A-6C show an example of time-domain nonlinear spin resonance signal extraction from the AF magnon mode in YFO. The same measurement can be used to estimate ZFS values in small molecules and large biomolecules. FIG. 6A shows spin resonances induced by THz pulse A ($B_A$) and THz pulse B ($B_B$) individually. FIG. 6B shows spin resonance ($B_{AB}$) induced by both THz pulse A and B at a delay of twice the period and the nonlinear response ($B_{NL}$ magnified 50×, magenta) extracted by $B_{NL}=B_{AB}-B_A-B_B$. FIG. 6C shows the Fourier transformation of the oscillatory part of $B_A$ in FIG. 6A and $B_{NL}$ in FIG. 6B revealing the linear and nonlinear magnetic resonance spectrum.

In FIGS. 6A-6C, the spin resonance signals $B_A$ and $B_B$ are measured using THz pulses denoted as A and B, individually. Each pulse induces the spin resonance signal shown as the sinusoidal oscillations following the main pulse. The spin resonance signal $B_{AB}$ is then measured using both THz pulses together with an inter-pulse delay τ as shown FIG. 6B. The nonlinear signal $B_{NL}$ shown as a function of time (t) in FIG. 6B was extracted as the difference signal $B_{NL}=B_{AB}-B_A-B_B$. The linear and nonlinear magnetic resonance spectra are shown in FIG. 6C, in which it can be seen that the background is suppressed in the nonlinear spectrum.

The background may be further suppressed in 2D magnetic resonance spectrum. In this case, the inter-pulse delay τ between THz pulses A and B can be incremented and the nonlinear signal $B_{NL}$ at each delay τ is measured to yield a 2D nonlinear time-domain signal $B_{NL}(\tau, t)$.

Figure 7:
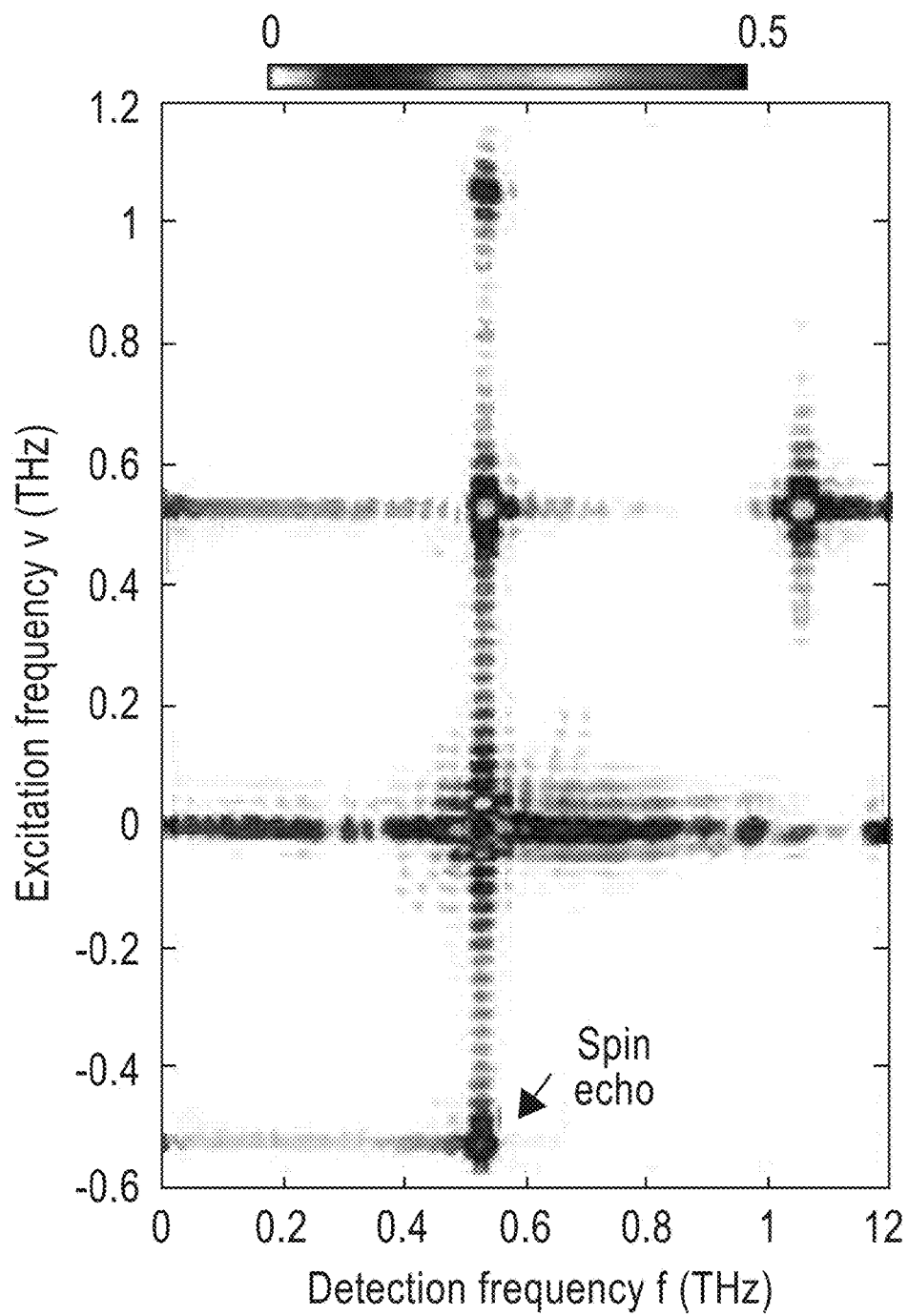
FIG. 7 shows 2D magnetic resonance spectrum of a spin resonance in $YFeO_3$(YFO).

FIG. 7 shows 2D magnetic resonance spectra of spin resonance in $YFeO_3$(YFO). The spectra are shown as a function of excitation frequency ν and detection frequency f, i.e., $B_{NL}(\nu, f)$. Amplitudes above 0.5 are saturated in the color map to bring out weak spectral features. The spectra shown in FIG. 7 is obtained via double Fourier transformation with respect to the inter-pulse delay τ and the detection time t. A spin echo spectral peak located at (ν=−0.527 THz, f=0.527 THz) is well separated from other nonlinear signals. The negative frequency value of ν denotes the phase of the signal radiated by spin precession that is generated by both incident pulses relative to the phase of the spin precession that is generated by the first incident pulse.

This technique can be applied to isolate the magnetic resonance signals from congested linear spectra and provide additional sensitivity to fine spectral signals for characterization of the biological subjects. For example, the high-spin Fe(II) ions present in hemoglobin in human blood are expected to exhibit ZFS values at THz frequencies. The Fe(II) ions in glycated hemoglobin may show a different ZFS value due to the difference in molecular structure. Therefore, these two types of hemoglobin may be differentiated by spectroscopic characterization of ZFS values. As THz light can penetrate human skins, this method provides a noninvasive characterization of human blood and diagnosis of diabetes directly on human body.

In some complexes of small molecules and biomolecules, the spins of electrons on multiple ions in close proximity interact with each other. The interaction strengths, or couplings, may be measured in the 2D spectrum because they lead to peaks in the spectrum in which the two frequency values are not equal; instead, one frequency value is equal to one spin transition frequency and the other frequency value is equal to the other spin transition frequency. These "off-diagonal" 2D spectral peaks can directly reveal spin-spin couplings and other features such as dynamical behavior, e.g. energy and coherence transfer between spins. Other 2D spectral peaks such as "2-quantum coherences" can also appear and can provide information about coupling between two coupled spin transitions that have the same frequency. These features appear with a frequency on the excitation frequency axis ν equal to the sum of two coupled transition frequencies.

Other features of the 2D spectra include "pump-probe" or transient absorption signals. Various characteristics such as the peak frequencies, strengths, linewidths, time-dependences, and dependences on applied pulse phases can be used to extract information about the underlying spin transitions, their couplings, and their dynamical behavior. All of these features can find useful applications in molecule characterization.

2D THz Magnetic Resonance Spectroscopy of Collective Spin Waves

Nonlinear manipulation of nuclear and electron spins is the basis for all advanced methods in magnetic resonance including multidimensional nuclear magnetic and electron spin resonance spectroscopies, magnetic resonance imaging, and in recent years, quantum control over individual spins. The methodology is facilitated by the ease with which the regime of strong coupling can be reached between radio frequency (RF) or microwave magnetic fields and nuclear or electron spins respectively. For example, the regime of strong coupling can be characterized by sequences of magnetic pulses that control the magnetic moment directions. The capabilities meet a bottleneck, however, for far-infrared magnetic resonances, which are characteristic of correlated electron materials, molecular magnets, and proteins that contain high-spin transition metal ions.

The development of 2D THz magnetic resonance spectroscopy and its use for direct observation of the nonlinear responses of collective spin waves (magnons) can address at least the bottleneck issue above. The spectra can show magnon spin echoes and 2-quantum signals that reveal pairwise correlations between magnons at the Brillouin zone center. They can also show resonance enhanced second-harmonic and difference-frequency signals. Methods described herein are readily generalizable to multidimensional magnetic resonance spectroscopy and nonlinear coherent control of terahertz-frequency spin systems in molecular complexes, biomolecules, and materials.

Electron spin resonances (ESR) in the terahertz (THz) frequency region can reveal rich information content in chemistry, biology, and materials science as described above. In molecular complexes and proteins, THz-frequency zero-field splitting (ZFS) of high-spin transition metal and rare earth ions show exquisite sensitivity to ligand geometries, providing mechanistic insight into catalytic function. With strong applied magnetic fields (e.g., about 10 tesla), resonances of unpaired electron spins in molecular complexes can be shifted from the usual microwave regime into the THz range, drastically improving the resolution of spectral splitting due to Zeeman interaction.

In many ferromagnetic (FM) and antiferromagnetic (AFM) materials, intrinsic magnetic fields in the same range put collective spin wave transitions in the THz range. Current ESR spectroscopy remains limited at THz frequencies because of the weak sources used, which allow measurements of free-induction decay (FID) signals that are linearly proportional to the excitation magnetic field strength, but not measurements of spin echoes and other nonlinear signals. This eliminates the possibility of two-dimensional (2D) THz ESR spectroscopy which, like 2D ESR at lower frequencies, could provide extensive insight into spin interactions and dynamics. For most proteins, even linear FID ESR signals may not be measurable because the THz spectrum includes much stronger absorption features due to low frequency motions of polar segments. However, the fast dephasing of such motions also ensures that these motions would not interfere with nonlinear spin echo signals. The extension of established, commercially available methodologies in multidimensional magnetic resonance spectroscopy to the THz frequency range can therefore find a wide range of applications spanning multiple disciplines.

Collective spin excitations in materials with spin order such as FM and AFM phases may be studied with weak THz fields, revealing the magnon frequencies through their FID signals and demonstrating linear superposition in the responses to time-delayed pulse pairs. In contrast, nonlinear coherent control and spectroscopy can unravel complex spin interactions in AFM-to-FM order switching, colossal magnetoresistance, and multi-ferroicity, and can enable new applications in quantum computing, nonvolatile memory, and spintronics at unprecedented time scales.

The nonlinearity of magnons can be explored using time-delayed THz pulse pairs with magnetic field strengths in excess of 0.1 tesla. 2D THz magnetic resonance spectroscopy can be understood in terms of multiple field-spin interactions that generate the nonlinear signal fields, similar to conventional 2D magnetic resonance but in the low-order perturbative regime. Magnons can be resonantly excited without promoting electrons to excited states (as in most spintronics excitation) and hence the observed nonlinearities are of purely magnetic origins.

Figure 8A:
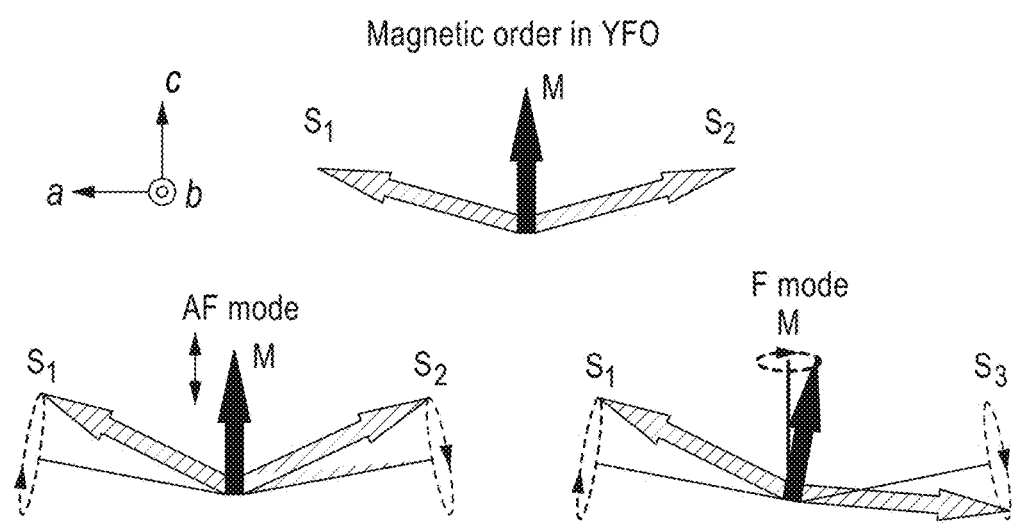
FIG. 8A illustrates magnetic order in YFO and two collective spin wave (magnon) modes in YFO including the AF and F modes.

For illustrating purposes, a single-crystal $YFeO_3$ (YFO) sample is used to characterize the 2D THz magnetic resonance spectroscopy method. FIG. 8A illustrates magnetic orders in YFO. The ground state has canted AFM order with a net magnetization. Two THz-active magnon modes, the quasi-AFM (AF) and quasi-FM (F) modes, can be constructed based on different cooperative motions of sublattice spins. The canted AFM order in YFO leads to a net magnetization M along the crystal c-axis. $S_1$ and $S_2$ are the high-spin Fe(III) electron spins ordered along the crystal a axis. The AF mode is the amplitude oscillation of M while the F mode the precession of M.

Macroscopically the AF mode corresponds to oscillation of the magnetization amplitude and the F mode corresponds to precession of the magnetization orientation. In YFO at room temperature, the AF mode at frequency $f_{AF}$=0.527 THz and the F mode $f_F$=0.299 THz can be selectively excited by THz pulses with magnetic field polarizations parallel and perpendicular respectively to the net magnetization direction. Upon THz excitation, magnons radiate FID signals B(t) at their resonance frequencies, revealing the linear-response spin dynamics in the material.

Figure 8B:
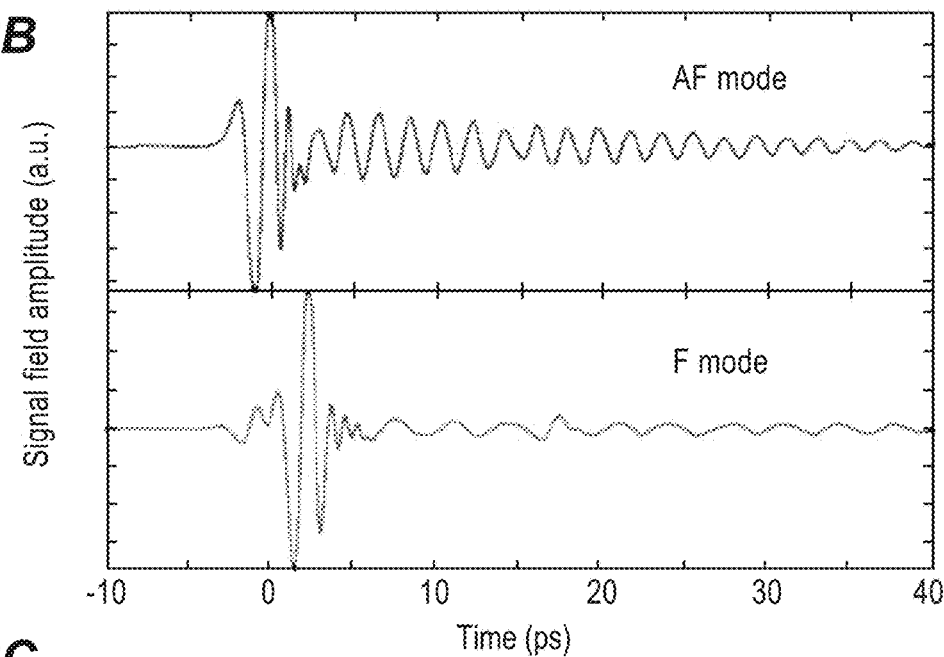
FIG. 8B shows spectra of single THz pulses transmitted through YFO followed by FID signals from the AF and F modes.
Figure 8C:
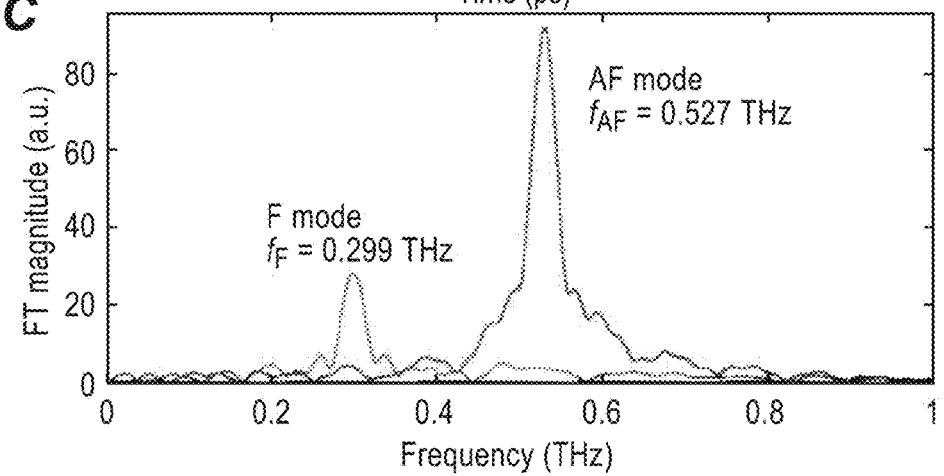
FIG. 8C shows Fourier transform magnitude spectra of the FID signals from the AF and F modes, showing magnon resonances at $f_{AF}$=0.527 THz and $f_F$=0.299 THz.

FIG. 8B shows spectra of single THz pulses transmitted through YFO followed by FID signals from the AF and F modes. FIG. 8C shows Fourier transform magnitude spectra of the FID signals from the AF and F modes, showing magnon resonances at $f_{AF}$=0.527 THz and $f_F$=0.299 THz.

Figure 9B:
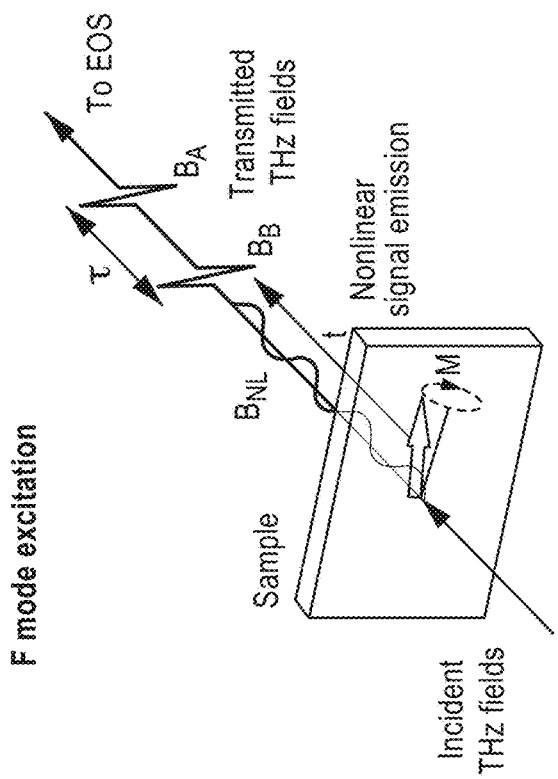
FIGS. 9A and 9B illustrate the interaction of THz pulses having parallel and perpendicular polarizations, respectively, with respect to a crystallographic axis of a single-crystal sample including YFO.
Figure 9A:
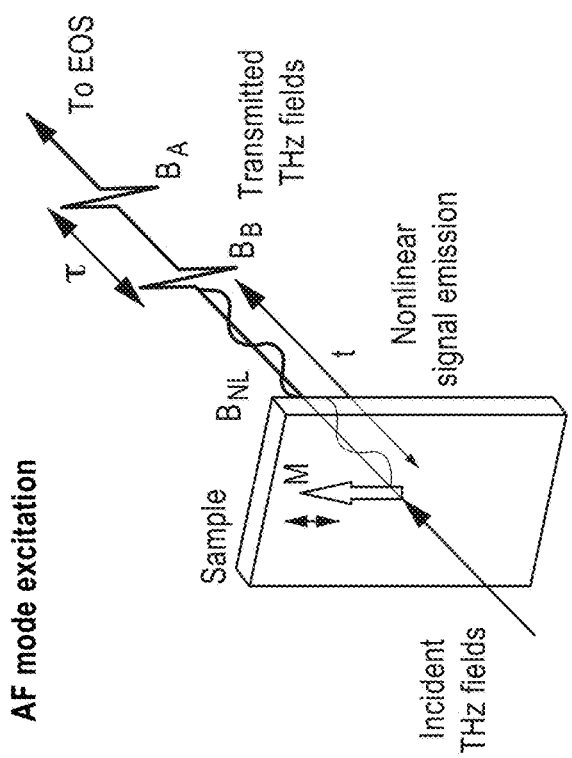

FIGS. 9A and 9B illustrate the interaction of THz pulses having parallel and perpendicular polarizations, respectively, with a sample. The two pulses have an inter-pulse delay τ and the sample has magnetization direction M. FIG. 9A illustrates excitation the AF mode and FIG. 9B illustrates the excitation of the F mode. Two collinearly propagating single-cycle THz magnetic fields $B_A$ and $B_B$ were focused onto the sample. The time delay τ between the two excitation pulses is incremented, and at each delay, the coherent time-dependent signal field B(τ, t) emerging from the sample by EOS is recorded.

A differential chopping detection scheme (see FIG. 2B) is used to isolate the nonlinear signal resulting from magnons interacting with both THz pulses. In the characterizations described here, the spectra of the two THz pulses are measured by electro-optic sampling (EOS) with a 1-mm thick GaP crystal. The field strength of the wo THz pulses are measured by EOS with a 0.1-mm thick GaP crystal (the thinner crystal yielded a smaller depolarized optical signal, ensuring that the signal was linearly proportional to the THz field). The first THz pulse (A) had a peak electric field strength of 420 kV/cm, while the second THz pulse had a peak electric field strength of 340 kV/cm. Both THz pulses had a usable bandwidth spanning from 0.1 to 2 THz. Due to the THz saturation and phase mismatch between the optical readout pulse and THz pulse in the GaP crystal, the main bandwidths were measured to be limited to about 0.1 THz to about 1 THz.

The pulse sequence used herein are implemented with a chopping detection method substantially similar to the one described with reference to FIG. 2.B. The laser repetition rate was 1 kHz. Two optical choppers denoted A and B were used to modulate the optical pulses that generated the corresponding THz pulses A and B at 250 Hz. On the first of four successive laser shots, the signal $B_B$ resulting from THz pulse B only was measured. On the second shot, the background noise was measured with neither THz pulse A nor B present. On the third shot, the signal $B_A$ from THz pulse A only was measured. On the fourth shot, the signal $B_{AB}$ generated by both THz pulses A and B was measured. The nonlinear signal B(τ, t) was extracted by subtracting the first three signals from the fourth at the specified inter-pulse delay τ and EOS measurement time t, averaging over multiple repetitions with the same time values and then scanning the values to cover the specified ranges of each.

FIGS. 10A-10C illustrate nonlinear signal extraction from signals measured by the differential chopping detection method. FIG. 10A shows AF mode magnon signals induced by THz pulse A (i.e., $B_A$) and THz pulse B (i.e., $B_B$) individually. FIG. 10B shows magnon responses (i.e., $B_{AB}$) with the presence of both THz pulse A and B at a delay τ of 3.7 ps (twice the period of the AF mode) and nonlinear response ($B_{NL}$ magnified by 50 times). The spike during the arrival of THz pulse B is due to nonlinear absorption induced by THz pulse A, which is excluded in all Fourier transformation in this work. FIG. 10C shows Fourier transformation of the oscillatory part in $B_{NL}$ revealing two spectral peaks at the fundamental and second harmonic magnon frequencies, which correspond respectively to the third- and second-order spectral peaks in the 2D spectrum.

In the trace of $B_{NL}$, a phase shift of $3\pi/2$ with respect to $B_{AB}$ and asymmetric distortion are noticeable. The phase shift corresponds to the phase of the third-order nonlinear response function. The asymmetric distortion is indicative of signals from second harmonic generation, which can be resolved in the Fourier transform spectrum of the oscillatory signal in $B_{NL}$, revealing peaks at $f_{AF}$ and $2f_{AF}$ as shown in FIG. 10C.

FIGS. 11A and 11B show normalized 2D time-time plots of $B_{NL}(\tau, t)$ from the AF mode and F mode, respectively. Amplitudes exceeding ±0.8 are saturated in the color map. The nonlinear signal field $B_{NL}$ is expressed as $B_{NL}(\tau, t) = B_{AB}(\tau, t) - B_A(\tau, t) - B_B(t)$, where $B_{AB}$ is the signal with both THz pulses present, and $B_A$ and $B_B$ are signals with THz pulse A and B present individually. Oscillations along the τ axis reveal the dependence of the nonlinear signal on particular frequency components of the incident THz fields, and oscillations along the t axis reveal the frequency components in the nonlinear signal field.

FIGS. 12A and 12B show experimental and simulated AF mode 2D magnitude spectra, respectively. Third-order spectral peaks include pump-probe (PP), nonrephasing (NR) rephasing (R), and 2-quantum (2Q) peaks. Second-order peaks include second harmonic generation (SHG) and THz rectification (TR) peaks.

FIGS. 12C and 12D show experimental and simulated F mode 2D magnitude spectra, respectively. These spectra show the full set of third-order peaks. All spectra are normalized and plotted according to the color scale shown.

2D Fourier transformation with respect to τ and t yields 2D spectra as functions of excitation frequency ν and detection frequency f as shown in FIGS. 12A and 12C for each magnon mode. The difference in phase accumulation of the induced magnon coherence during time periods τ and t allows the 2D spectra to be separated into nonrephasing (NR) and rephasing (R) quadrants with correspondingly positive and negative excitation frequencies. Along zero excitation frequency there is a pump probe (PP) spectral peak which results from THz-field-induced magnon population without phase accumulation.

The 2D spectrum for each magnon mode shows the complete set of third-order nonlinear signals. The R (spin echo) peak and NR peak each result from a single field interaction during pulse A that creates a first-order magnon coherence. After delay τ, two field interactions during pulse B generates a magnon population, and then a third-order magnon coherence (either phase reversed or not relative to the first-order coherence) radiates the nonlinear signal. The 2-quantum (2Q) peak arises from two field interactions during pulse A that create a 2-quantum coherence (2QC). After time τ, one field interaction during pulse B induces transitions to a third-order 1-quantum coherence that radi-ates the signal. The 2QC reveals correlations between pairs of zone-center magnons (distinct from zone-boundary magnon correlations revealed in two-magnon Raman spectra).

Figure 13A:
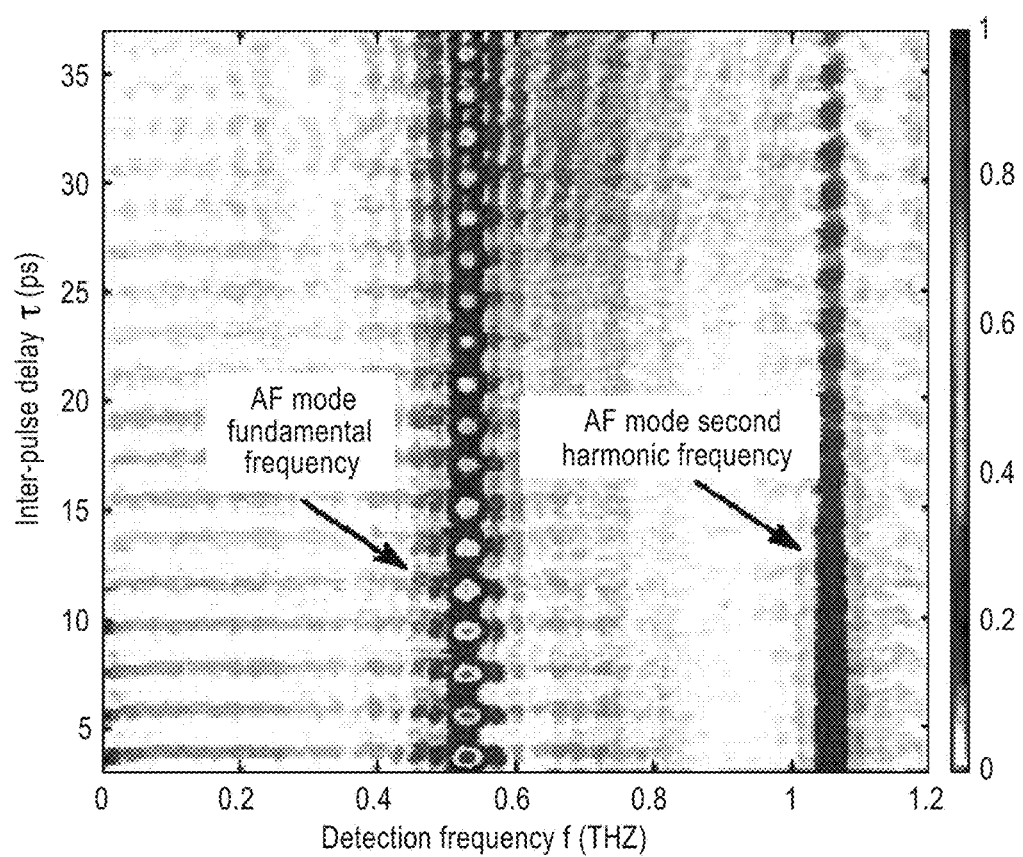
FIGS. 13A-13G illustrate 2D time-frequency plot of AF magnon mode nonlinear response.
Figure 13B:
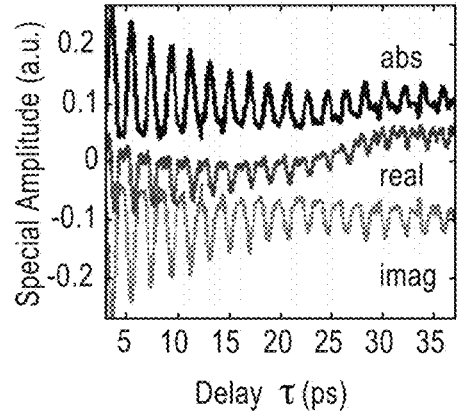
Figure 13C:
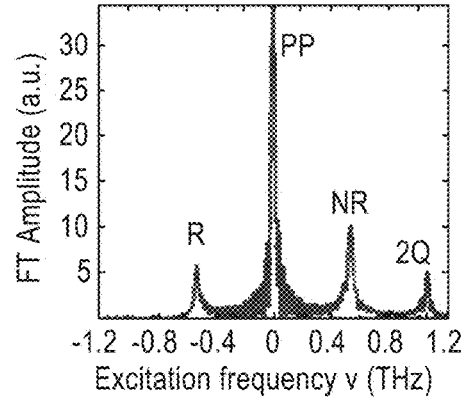

FIGS. 13A-13G illustrate 2D time-frequency plot of AF magnon mode nonlinear response. FIG. 13A shows 2D time frequency plot $B_{NL}(\tau,f)$ generated by a numerical Fourier transformation along t of the 2D time-time plot from the AF magnon mode shown in FIG. 11A. The AF mode fundamental and second harmonic peaks are modulated as the delay τ increases. FIG. 13B shows spectral modulation as a function of τ at the AF mode frequency $f=f_{AF}$. The real part, imaginary part, and absolute value of the complex spectral peak are plotted. Oscillations are clearly discernible in the traces, showing a modulation of the spectral amplitude and phase as a function of τ. FIG. 13C shows Fourier transformation of the complex spectral modulation along τ in FIG. 13B yielding the spectrum as a function of ν, which is equivalent to taking a spectral slice along $f=f_{AF}$ in the 2D spectrum in FIG. 12A. Four peaks are observed in the spectrum, corresponding to the rephasing (R), nonrephasing (NR), 2-quantum coherence (2Q), and pump-probe (PP) peaks.

Figure 13D:
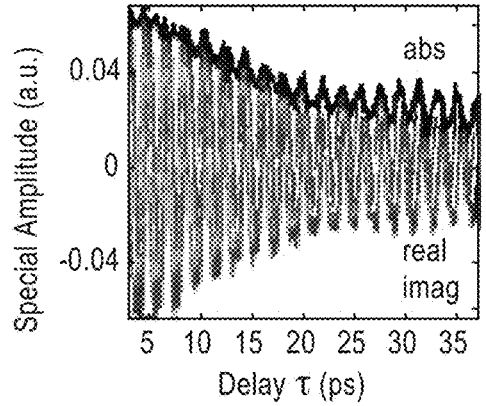
Figure 13E:
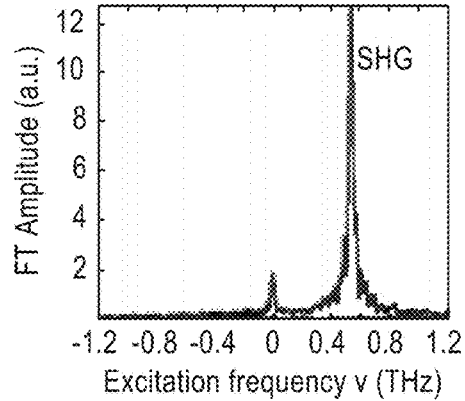

FIG. 13D shows spectral modulation as a function of τ along $f=f_{AF}$. The real part, imaginary part, and absolute value of the complex spectral modulation are plotted as functions of τ. FIG. 13E shows Fourier transformation of the complex spectral peak modulation along τ in FIG. 13D yielding the spectrum as a function of ν, which is equivalent to taking a spectral slice along $f=2f_{AF}$, the magnon second harmonic frequency, in the 2D spectrum in FIG. 12A.

Figure 13F:
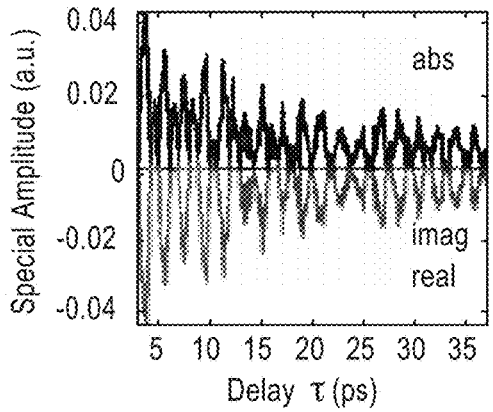
Figure 13G:
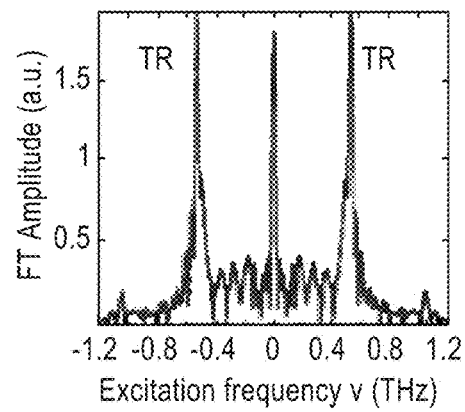

FIG. 13F shows spectral modulation as a function of τ at f=0 THz. The real part, imaginary part, and absolute value of the complex spectral peak are plotted as functions of t FIG. 13G shows Fourier transformation of the spectral peak modulation along τ yielding the spectrum as a function of ν, which is equivalent to taking a spectral slice along f=0 in the 2D spectrum in FIG. 12A.

As the delay τ between the two THz pulses varies, the amplitudes and phases of the two peaks are modulated as shown in FIG. 13A, revealing their correlation to the magnon coherence induced by THz pulse A. Fourier transformation of the frequency-time plot with respect to inter-pulse delay τ yields the observed 2D spectrum of the AF mode magnons. It can be seen that the spectral peak at the AF mode fundamental frequency in FIG. 10C includes all of the R, NR, 2Q, and PP peaks in the 2D spectrum; the peak at the AF mode second harmonic frequency is the SHG peak; and the peak at zero frequency is the TR peak.

In the 2D time-domain traces in FIGS. 11A and 11B, observed signals due to THz pulse double reflections (from double reflections of the laser pulse in a beam splitter delayed from each main THz pulse by ~15 ps) were not eliminated by the differential chopping detection method. But these signals did not have noticeable effects the on observed spectral responses Fourier transformed from the selected time windows. Double reflections of THz pulses in the sample (delayed from the main pulse by ~67 ps) reen-tered the sample and provided additional field magnon interactions to generate stimulated nonlinear signals which were not eliminated but were excluded in the selected time windows.

Figures 14A, 14B:
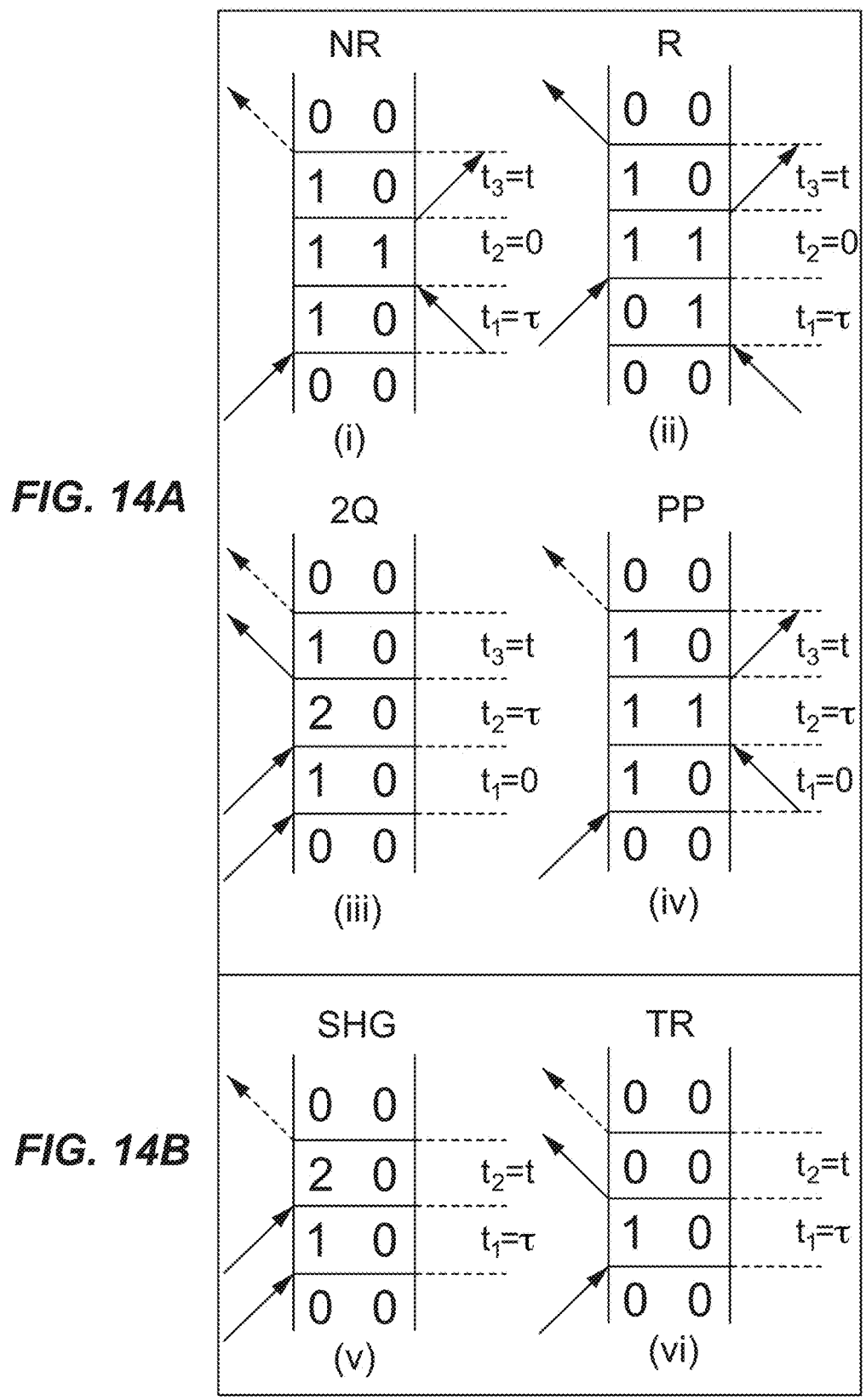
FIGS. 14A and 14B show double-sided Feynman diagrams illustrating typical excitation pathways leading to the coherent emission of third-order and second order nonlinear signals, respectively.

FIGS. 14A and 14B show double-sided Feynman diagrams illustrating typical excitation pathways leading to the coherent emission of third-order (a, (i)-(iv)) and second order (b, (v)-(vi)) nonlinear signals, respectively. Each solid arrow denotes a field interaction that induces a transition between magnon populations or coherences denoted by diagonal (|0><0|, |1><1|) or off diagonal (|1><0|, 2><0|) density matrix elements respectively. The dashed arrows represent the measured signal fields. The time interval subscripts denote the number of preceding field interactions.

The pump-probe signal is generated by two field interactions during pulse A that create magnon population and, after delay τ, one interaction with pulse B that generates a third-order coherence that radiates the signal. These spectral peaks due to three field magnon interactions are represented concisely by the Feynman pathways shown in the diagrams (i)-(iv) in FIG. 14A. In addition, second-order spectral peaks due to THz second harmonic generation and THz rectification are also identified in the AF mode 2D spectrum. The corresponding Feynman pathways are shown in diagrams (v)-(vi) in FIG. 14B. Second-order nonlinear processes are ordinarily forbidden in a centrosymmetric crystal, but are observed in YFO. The second-order nonlinearity originates from the large-angle precession of each sublattice spin as the spin system is inherently saturable and the precession of each sublattice spin does not cancel along the direction of the net magnetization M.

To gain further insight into the underlying physics we performed simulations based on the Landau-Lifshitz-Gilbert (LLG) equation. The Hamiltonian is written as $$H = JS_1 \cdot S_2 + D \cdot (S_1 \times S_2) - \Sigma_{i=1}^{2}(K_x S_{ix}^2 + K_z S_{iz}^2) - \gamma(B_A(\tau,t) + B_B(t)) \cdot \Sigma_{i=1}^{2} S_i \quad (1)$$

The first term describes the AFM coupling between neighboring spins $S_1$ and $S_2$ with a positive exchange constant J. The second term derives from the DM interaction with the antisymmetric exchange parameter D being a vector. The interplay between them results in the canted AFM ground state. The third term accounts for the crystalline anisotropy. The last term is the Zeeman interaction between spins and THz magnetic fields.

From the Hamiltonian, a time-dependent effective magnetic field can be calculated by $$B_i^{eff} = -\frac{1}{\gamma} \frac{\partial H}{\partial S_i}$$

for each sublattice i=1, 2 and enters the coupled LLG equation as:

$$\frac{dS_i}{dt} = \frac{\gamma}{1+\alpha^2}\left[S_i \times B_i^{eff} + \frac{\alpha}{|S_i|} S_i \times (S_i \times B_i^{eff})\right] \quad (2)$$

where the gyromagnetic ratio $\gamma = g\mu_B/\hbar$ is negative in our convention and the damping parameter is chosen as $\alpha = 1.3 \times 10^{-3}$ and $5.5 \times 10^{-4}$ for the AF and F modes to best match the experimental results. Numerically solving equation (2) with realistic material parameters as a function of time variables τ and t yields the dynamics of the sub lattice spins and hence of the net magnetization.

Numerically solving the LLG equation can obtain vectorial solutions of the net magnetization $M \sim S_1 + S_2$ at different THz magnetic field polarizations. The nonlinear temporal responses of |M| and Mb can be extracted to represent the AF and F mode magnons respectively. 2D Fourier transformation yielded the simulated 2D spectra of each magnon shown in FIGS. 12B and 12D, exhibiting excellent agreement with the experimental results and confirming their magnetic origins. Comparing simulations with and without the DM interaction (i.e. canted AFM ground state versus AFM ground state) leads to the observation that the second-order responses of the AF mode were observed only with the DM term, which conforms to the fact that the second-order nonlinearity resulting from the inherently saturable net magnetization from the canted AFM order. The second-harmonic and rectification signals are due to large-angle spin precessions, yet rectification signals have not been observed before.

Figure 15A:
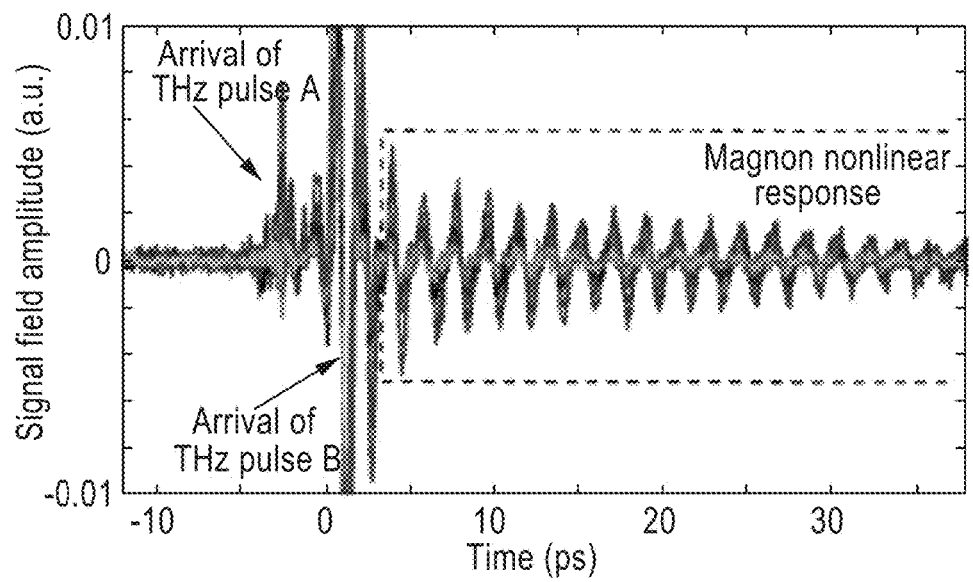
FIG. 15A shows time-domain trace of $B_{NL}$ at varying strengths of the excitation THz magnetic fields. The oscillatory signals in the dashed box are the nonlinear magnon responses.
Figure 15B:
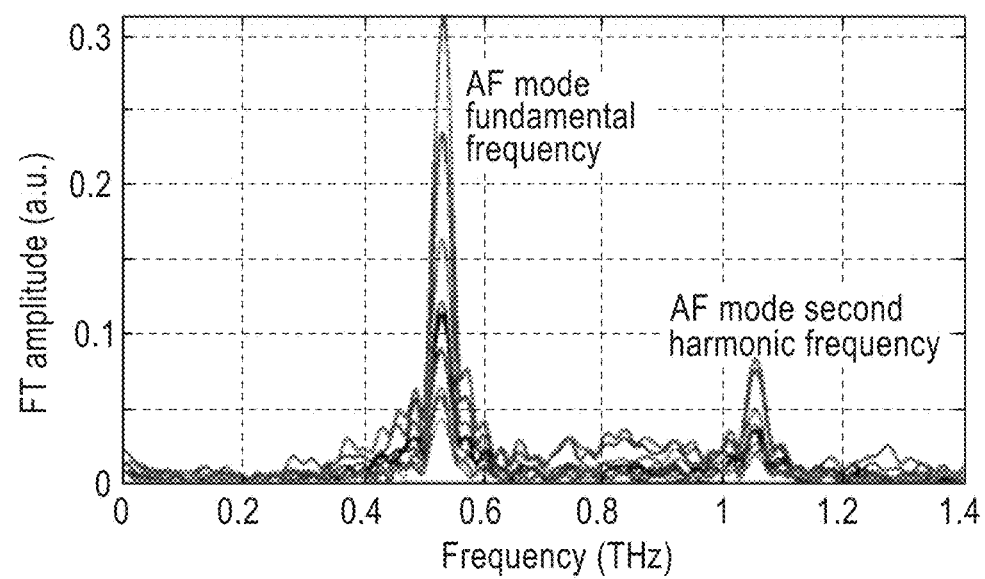
FIG. 15B shows Fourier transformation magnitude spectra of the oscillatory signals show in FIG. 15A.

FIG. 15A shows time-domain trace of $B_{NL}$ at varying strengths of the excitation THz magnetic fields. The oscillatory signals in the dashed box are the nonlinear magnon responses. FIG. 15B shows Fourier transformation magnitude spectra of the oscillatory signals show in FIG. 15A. Two spectral peaks at the fundamental and second harmonic frequencies of the AF mode are observed. There is also a weak peak at zero frequency.

In the characterization, the nonlinear time-domain traces of $B_{NL}$ at a delay of τ=3.7 ps was measured while varying THz magnetic field strengths to the same extent by attenuating the input pump laser intensity. The data are shown in FIG. 15A. The nonlinear signal excluding that at during the arrival of THz pulse B was Fourier transformed to yield the frequency-domain responses shown in FIG. 15B, where two spectral peaks at the fundamental and second harmonic frequencies of the AF mode are present. Due to the low signal-to-noise ratio around zero frequency, the THz rectification peak is not clearly discerned.

Figure 16:
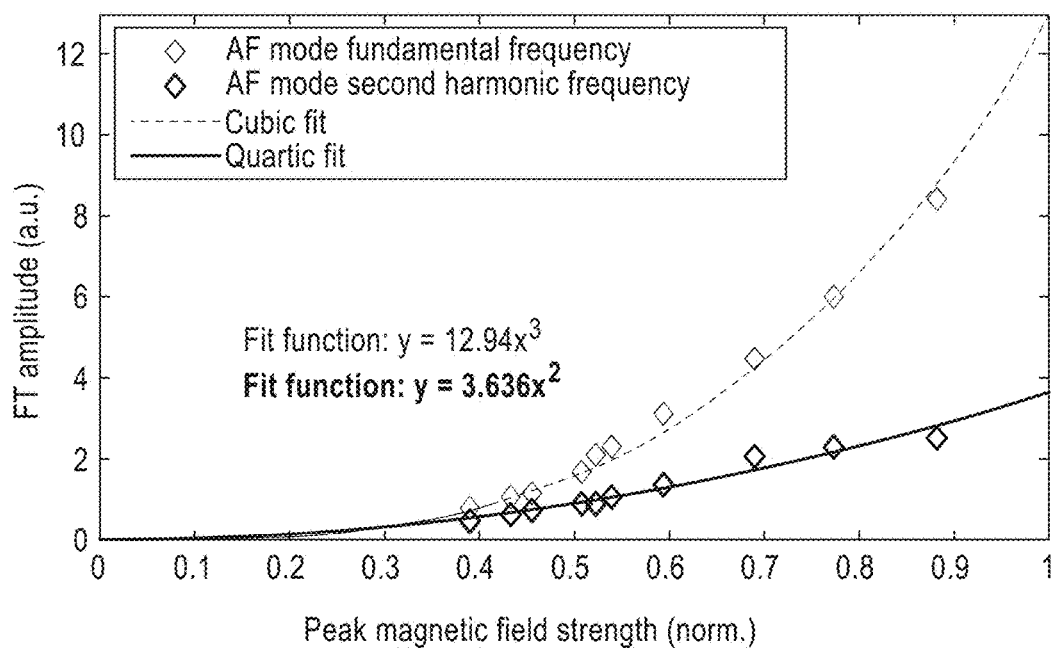
FIG. 16 shows peak amplitudes in 2D THz spectroscopy as a function of the input THz magnetic field strength.

FIG. 16 shows dependence of the amplitudes of spectral peaks as a function of the input THz magnetic field strength. The peaks at the AF mode fundamental and second harmonic frequencies are fitted with one fit parameter to cubic and quadratic power dependences respectively. The scaling relations with respect to the input peak THz magnetic field strength confirm the orders of the nonlinear signals observed in the experiments. The spectrum near the peak amplitude of the spectral peaks at fundamental can be integrated with the second harmonic magnon frequencies and plotted as a function of the input THz magnetic field strength, as shown in FIG. 16. The integrated spectral amplitude at the fundamental frequency has a cubic dependence on the input THz magnetic field strength, while that at the second harmonic frequency shows a quadratic field dependence. The scaling behaviors further confirm that the spectral peaks observed in the 2D spectra are of third- and second-order respectively.

It can be instructive to consider the origins of the second-order signals. As shown in FIG. 8A, the AF mode involves counter-rotating magnetization components $S_1$ and $S_2$. During each cycle, both vectors can reach their maxima and minima along the M direction (i.e., c crystallographic axis) at the same times, but their components along the b crystallographic axis can have opposite signs. The magnitude of each vectors typically does not change as it precesses about its initial location. Its maximum and minimum values along c axis therefore can lie equidistant from its initial location along an arc, whose slope is steeper below the initial location than above it. As seen in FIGS. 17A-17D below, the magnitude of each vectors therefore increases its value along c at its maximum by less than it decreases its value along c at its minimum, relative to its static value. The time-dependence of the c-component is not sinusoidal. The same amount of time is spent above and below the initial location during each full cycle, but the positive and negative amplitudes are not equal. The distorted periodic dependence includes DC and second harmonic components, which radiate the second harmonic and rectification signals respectively.

FIGS. 17A-17D illustrate temporal evolution of sublattice spins in AF magnon mode. FIG. 17A shows exaggerated precession of sub-lattice spins $S_1$ and $S_2$ on the Poincare sphere. The two arrows denote $S_1$ and $S_2$ precessing around their static orientations indicated by the light lines. The black arrow denotes the net magnetization M. The dashed ellipses are the trajectory of $S_1$ and $S_2$ on the sphere surface. Under large angle precession, the excursion along b axis is considerable, and the actual trajectories are distorted ellipses. The static orientations of spins do not point to the center of the ellipses. The first bottom figure in FIG. 17A (i.e., FIG(i)) shows the orientation of the sublattice spins in equilibrium. The second and third bottom figures (i.e., (ii) and (iii)) show the maximum and minimum excursions of the orientation of the sublattice spins away from the orientation at equilibrium. FIG. 17C shows the sinusoidal change in the projection of $S_1$ and $S_2$ along crystal c axis, $S_{1,c}$ as a function of time t normalized to the precession period T. FIG. 17D shows the second harmonic component of the change in $S_{1,c}$ and a DC offset. FIG. 17B shows temporal evolution of $S_{1,c}$ considering precession at the fundamental frequency (in FIG. 17C) and second harmonic frequency (in FIG. 17D), and a DC offset (black shown in FIG. 17D). It shows that $S_{1,c}$ spends more time below the static orientation and less time above. This distorted evolution of $S_{1,c}$ gives rise to the second harmonic and rectification signals in M.

Note that the second harmonic signal is derived from a 2QC, as shown in the Feynman diagram in FIG. 14B(v). A third incident field can induce a transition down to a 1 QC that radiates a third-order signal. That is the 2Q signal depicted in FIG. 14A(iii). The two diagrams show the same result after the first two field interactions. They can be viewed as resulting from interactions between magnon pairs at the Brillouin zone center. As the magnon amplitude becomes infinitesimally small, the positive and negative amplitudes along c become equal. At finite amplitudes, the moments of individual magnons interact, giving rise to the observed nonlinearities.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus for nonlinear terahertz (THz) spectroscopy, the apparatus comprising:
    a THz radiation source to illuminate a sample with a plurality of THz pulses, the plurality of THz pulses comprising:
        a first copy of a first THz pulse;
        a first copy of a second THz pulse; and
        a pulse train including a second copy of the first THz pulse and a second copy of the second THz pulse separated by an inter-pulse delay τ, the pulse train inducing an electron spin resonance (ESR) in the sample;
    a detector, in optical communication with the sample, to generate:
        a first signal $B_A$ representing a response of the sample to the first copy of the first THz pulse;
        a second signal $B_B$ representing a response of the sample to the first copy of the second THz pulse; and
        a third signal $B_{AB}$ representing a response of the sample to the pulse train; and
    a processor, operably coupled to the detector, to estimate a nonlinear ESR response $B_{NL}$ of the sample to the pulse train based on the first signal $B_A$, the second signal $B_B$, and the third signal $B_{AB}$.

2. The apparatus of claim 1, wherein the plurality of THz pulses has a wavelength of about 0.1 THz to about 20 THz.

3. The apparatus of claim 1, wherein the inter-pulse delay τ is about 0 ps to about 100 ps.

4. The apparatus of claim 1, wherein the THz radiation source comprises:
    a laser to emit a plurality of optical pulses; and
    a nonlinear crystal, in optical communication with the laser, to generate the plurality of THz pulses by optically rectifying the plurality of optical pulses.

5. The apparatus of claim 4, wherein the THz radiation source further comprises:
    at least one delay stage, in optical communication with the laser, to delay a first optical pulse in the plurality of optical pulses with respect to a second optical pulse in the plurality of optical pulses so as to generate the inter-pulse delay τ.

6. The apparatus of claim 4, wherein the nonlinear crystal comprises $LiNbO_3$.

7. The apparatus of claim 1, wherein the detector comprises:
    an electro-optic crystal to receive the plurality of THz pulses, the plurality of THz pulses generating a time-dependent birefringence in the electro-optical crystal; and
    an optical detector, in optical communication with the electro-optical crystal, to detect a plurality of optical probe pulses transmitted through the electro-optical crystal, the plurality of optical probe pulses having polarizations that vary in response to the time-dependent birefringence.

8. The apparatus of claim 7, wherein the electro-optical crystal comprises a GaP crystal.

9. The apparatus of claim 1, wherein the processor is configured to estimate at least one of a zero-field splitting (ZFS) or a spin-spin interaction strength of the sample based on the nonlinear ESR response BNL.

10. The apparatus of claim 9, wherein the processor is configured to estimate the at least one of the ZFS or the spin-spin interaction strength of the sample based on the nonlinear ESR response BNL.

11. The apparatus of claim 1, wherein the THz radiation source is configured to change the inter-pulse delay τ so as to generate a two dimensional (2D) nonlinear ESR signal BNL(t, τ), where t is time, and wherein the processor is configured to perform a two-dimensional (2D) Fourier transform of the 2D nonlinear ESR signal $B_{NL}$(t, τ) with respect to the time t and the inter-pulse delay τ.

12. A method of nonlinear terahertz (THz) spectroscopy, the method comprising:
    illuminating a sample with a first copy of a first THz pulse;
    generating a first signal BA representing a response of the sample to the first copy of the first THz pulse;
    illuminating the sample with a first copy of a second THz pulse;
    generating a second signal BB representing a response of the sample to the first copy of the second THz pulse;
    illuminating the sample with a pulse train including the a second copy of the first THz pulse and a second copy of the second THz pulse, separated by an inter-pulse delay r, the pulse train inducing an electron spin resonance (ESR) in the sample;
    generating a third signal BAs representing a response of the sample to the pulse train; and
    estimating a nonlinear ESR signal BNL based on the first signal BA, the second signal BB, and the third signal BAs.

13. The method of claim 12, wherein illuminating the sample with the first copy of the first THz pulse comprises transmitting the first copy of the first THz pulse at a wavelength of about 0.1 THz to about 10 THz.

14. The method of claim 12, wherein illuminating the sample with the pulse train comprises transmitting the second copy of the second THz pulse about 0 ps to about 100 ps after transmitting the second copy of the first THz pulse.

15. The method of claim 12, wherein illuminating the sample with the first copy of the first THz pulse comprises illuminating at least one of a transition metal ion or a rare earth ion.

16. The method of claim 12, wherein illuminating the sample with the first copy of the first THz pulse comprises illuminating glycated hemoglobin.

17. The method of claim 12, further comprising generating the first copy of the first THz pulse by transmitting an optical pulse through a nonlinear crystal via optical rectification.

18. The method of claim 17, wherein transmitting the optical pulse comprises transmitting the optical pulse through a $LiNbO_3$ crystal.

19. The method of claim 12, wherein generating the first signal comprises:

transmitting the first THz pulse through an electro-optical crystal to generate a time-dependent birefringence in the electro-optical crystal; and detecting an optical probe pulse transmitted through the electro-optical crystal so as to generate the first signal $B_A$.

20. The method of claim 12, further comprising:
estimating at least one of a zero-field splitting (ZFS) or a spin-spin interaction strength of the sample based on the nonlinear ESR signal $B_{NL}$.

21. The method of claim 20, wherein estimating the at least one of the ZFS or the spin-spin interaction strength of the sample comprises performing a Fourier transform of the nonlinear ESR signal BNL.

22. The method of claim 12, further comprising: changing the inter-pulse delay τ so as to generate a two-dimensional (2D) nonlinear ESR signal BNL(t, τ), where τ is time; and performing a two-dimensional (2D) Fourier transform of the 2D nonlinear ESR signal Bnl(t, τ) with respect to the time t and the inter-pulse delay τ.

23. A system for nonlinear terahertz (THz) spectroscopy, the system comprising:

a THz radiation source illuminate a sample with a plurality of THz pulses, the plurality of THz pulses comprising a plurality of THz pulse groups and an ith THz pulse group in the plurality of THz pulse groups comprising:

a first copy of a first THz pulse;

a first copy of a second THz pulse; and a pulse train including a second copy of the first THz pulse and a second copy of the second THz pulse separated by an inter-pulse delay $\tau_i$, where i is a positive integer, the pulse train inducing an electron spin resonance (ESR) in the sample;

a detector in optical communication with the sample, for the ith THz pulse group in the plurality of THz pulse groups, the detector generating:

a first signal $B_A(t, \tau_i)$ representing a response of the sample to the first copy of the first THz pulse, where t is time;

a second signal $B_B(t, \tau_i)$ representing a response of the sample to the first copy of the second THz pulse; and a third signal $B_{AB}(t, \tau_i)$ representing a response of the sample to the pulse train; and a processor, operably coupled to the detector, to estimate a nonlinear ESR signal BNL for the ith THz pulse group based on the first signal $B_A(t, \tau_i)$, the second signal $B_B(t, \tau_i)$, and the third signal $B_{AB}(t, \tau_i)$, the processor further performing a 2D Fourier transform to the nonlinear ESR signal $B_{NL}(t, \tau_i)$ with respect to the time t and the inter-pulse delay $\tau_i$ so as to estimate at least one of a zero-field splitting (ZFS) or a spin-spin interaction strength of the sample.

* * * * *